United States Patent [19]

Domagala et al.

[11] Patent Number: 5,585,491
[45] Date of Patent: Dec. 17, 1996

[54] ANTIBACTERIAL AGENTS

[75] Inventors: John M. Domagala, Canton; Susan E. Hagen, Canton Township; John S. Kiely, Ann Arbor, all of Mich.

[73] Assignee: Otsuka Pharmaceutical Co., Ltd., Tokyo, Japan

[21] Appl. No.: 527,199

[22] Filed: Sep. 12, 1995

Related U.S. Application Data

[60] Division of Ser. No. 862,152, Apr. 7, 1992, abandoned, which is a continuation-in-part of Ser. No. 798,296, Nov. 25, 1991, abandoned, which is a division of Ser. No. 280,924, Dec. 9, 1988, Pat. No. 4,920,120, which is a continuation-in-part of Ser. No. 147,462, Jan. 25, 1988, abandoned.

[51] Int. Cl.$^6$ .................. A61K 31/435; C07D 471/02
[52] U.S. Cl. ................................................ 546/123
[58] Field of Search .................. 546/156, 123; 514/300

[56] References Cited

U.S. PATENT DOCUMENTS

| | | | |
|---|---|---|---|
| 3,753,993 | 8/1973 | Lesher et al. | 546/156 |
| 3,907,808 | 9/1975 | Lesher et al. | 546/156 |
| 4,146,719 | 3/1979 | Irikura | 544/363 |
| 4,341,784 | 7/1982 | Matsumoto et al. | 514/300 |
| 4,448,962 | 5/1984 | Irikura et al. | 544/362 |
| 4,571,396 | 2/1986 | Hutt et al. | 514/246 |
| 4,649,144 | 3/1987 | Matsumoto et al. | 514/300 |
| 4,684,648 | 8/1987 | Tone et al. | 514/249 |
| 4,704,459 | 11/1987 | Todo et al. | 546/123 |
| 4,725,595 | 2/1988 | Schriewer et al. | 514/211 |
| 4,762,831 | 8/1988 | Grohe et al. | 514/230.2 |
| 4,772,706 | 9/1988 | Wemple et al. | 544/349 |
| 4,774,246 | 9/1988 | Chu | 514/254 |
| 4,923,879 | 5/1990 | Hutt et al. | 514/300 |

FOREIGN PATENT DOCUMENTS

| | | |
|---|---|---|
| 0207420 | 1/1987 | European Pat. Off. . |
| 0242789 | 10/1987 | European Pat. Off. . |
| 0287951 | 9/1988 | European Pat. Off. . |
| 0326891 | 8/1989 | European Pat. Off. . |
| 0387802 | 9/1990 | European Pat. Off. . |
| 61-85349 | 4/1986 | Japan . |
| 62-00045 | 1/1987 | Japan . |
| 1208279 | 10/1970 | United Kingdom . |

OTHER PUBLICATIONS

J. of the American Chem. Soc., vol. 97, No. 25, 1975, pp. 7383–7385: A. I. Meyers et al.,; "Oxazolines, XXII. Nucleophilic aromatic substitution on aryl oxazolines. An efficient approach to unsymmetrically substituted biophenyls and o–alkyls benzoic acids".

Chemical Abstracts, vol. 84, No. 3, Mar. 19, 1976, Columbus, Ohio, US: T. N. Gerasimova et al.; "Interaction of pentaflurobenzoic acid and its esters with alkylmagnesium halides," p. 425, Abstract No. 16902r.

Bulletin of the Chem. Soc. of Japan, vol. 57, 1984, pp. 225–231: Y. Inukai et al.; "Ortho–distributed f–benzenes. V. Intramolecular heteroatomfaciliated ortho–substitution of f–benzene derivatives with oxazolinyl and oxazinyl groups".

Patent Abstracts of Japan, Sep. 4, 1986, vol. 10, No. 258, (C–370) (2314).

Patent Abstracts of Japan, May 28, 1987, vol. 11, No. 167, (C–425) (2614).

Chemical Abstracts, vol. 116, No. 11, 16 Mar. 1992, Abstract No. 106129c, D. Bouzard et al.

Miyamoto et al., "Pyridonecarboxylic Acids as Antibacterial Agents", VIII. [Chem. Pharm. Bull., 35(6)2280–2285 (1987)].

J. Med. Chem., 23:1358–1363, 1980, H. Koga et al., "Structure–Activity Relationships of Antibacterial 6,7–and 7,8–. . .".

Eur. J. Med. Chem. –Chimica Therapeutica, Jan.–Feb., 1977–12, No. 1, p.27, C. Rufer et al., "Chinoloncarbonsauren . . .".

Chem. and Pharm. Bulletin, vol. 35, No. 6, 1987, pp. 2280–2285, T. Miyamoto et al.: "Pyridonecarboxylic acids as antibacterial agents. VIII. An alternative synthesis of enoxacin via fluoronicotinic acid derivatives".

*Primary Examiner*—Bernard Dentz
*Attorney, Agent, or Firm*—Finnegan, Henderson, Farabow, Garrett & Dunner, L.L.P.

[57] ABSTRACT

Novel naphthyridine-, and quinolinecarboxylic acids as antibacterial agents are described as well as methods for their manufacture, formulation, and use in treating bacterial infections including the description of certain novel intermediates used in the manufacture of the antibacterial agents.

10 Claims, No Drawings

ANTIBACTERIAL AGENTS

CROSS-REFERENCE TO RELATED APPLICATION

This is a of divisional application Ser. No. 07/862,152, filed Apr. 7, 1992, now abandoned which is a continuation-in-part of application Ser. No. 07/798,296, filed Nov. 25, 1991 now abandoned, which is a divisional application of Ser. No. 07/280,924, filed Dec. 9, 1988, now U.S. Pat. No. 4,920,120, which is a continuation-in-part of application Ser. No. 07/147,462, filed Jan. 25, 1988 now abandoned.

BACKGROUND OF THE INVENTION

U.S. Pat. No. 4,341,784 discloses certain substituted 7-(3-amino-1-pyrrolidinyl)-1-ethyl-6-fluoro-1,4-dihydro-4-oxo-1,8-naphthyridine-3carboxylic acids having the general formula:

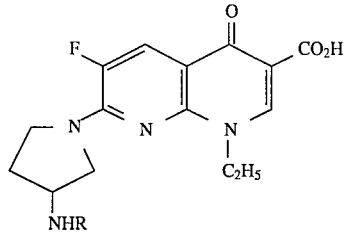

The compounds are disclosed to have antibacterial activity.

The Journal of Medicinal Chemistry, 23, 1358 (1980) discloses certain substituted quinoline-3-carboxylic acids having the structural formula

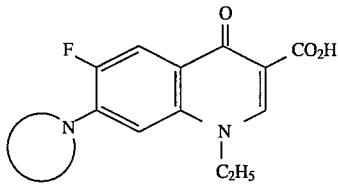

wherein

may be pyrrolidinyl. See also U.S. Pat. No. 4,146,719. The compounds are disclosed to have antibacterial activity.

Certain 7-heterocyclic substituted 1,8-naphthyridines are disclosed in Eur. J. Med. Chem.—Chemica Therapeutica, 29, 27 (1977). U.S. Pat. Nos. 3,753,993 and 3,907,808 disclose certain 7-pyridylquinolones.

European Patent Applications 229,635 and 206,101 cover certain 1,8-bridged-1,4-dihydro-4-quinolinones having the formula

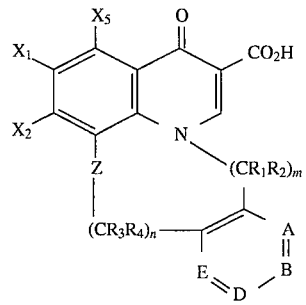

wherein $X_1$ is hydrogen, $NO_2$, 1–3C alkyl or halogen; $X_2$ is halogen, 1–3C-alkyl, 1–3C-alkylsulphenyl or optionally substituted phenylsulphenyl; $X_5$ is hydrogen, halogen or methyl.

U.S. Pat. No. 4,774,246 discloses certain substituted 1-phenyl-6,8-difluoro-1,4-dihydro-4-oxo-7-(1-piperazinyl)-quinoline-3-carboxylic acid of general formula

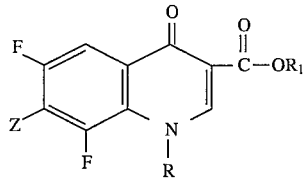

U.S. Pat. No. 4,704,459 discloses a process for certain 1-substituted aryl-1,4-dihydro-4-oxonaphthyridine derivatives of general formula

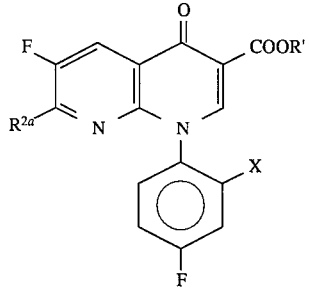

U.S. Pat. No. 4,649,144 discloses certain 1,8-naphthyridine derivatives of general formula

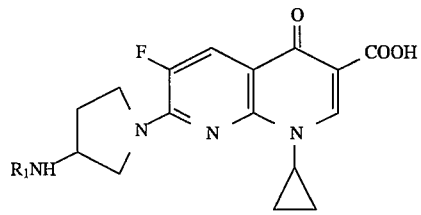

U.S. Pat. No. 4,571,396 discloses certain naphthyridine-, quinoline-, and benzoxazine-carboxylic acids with a bridged side-chain at the seven-position.

U.S. Pat. No. 4,923,879 discloses certain naphthyridine-, quinoline-, and benzoxazine-carboxylic acids with a bridged side-chain at the seven-position and a hydrogen, fluoro or amino at the five-position.

The references teach that these compounds possess antibacterial activity.

SUMMARY OF THE INVENTION

One aspect of the present invention is a compound of Formula I

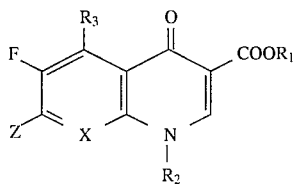

or a pharmaceutically acceptable acid addition or base salt thereof wherein Z is

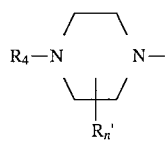

or

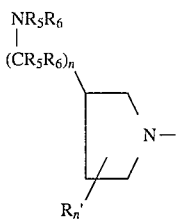

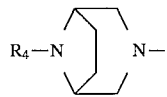

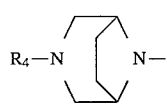

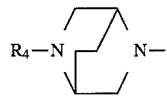

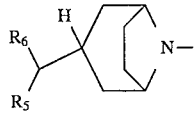

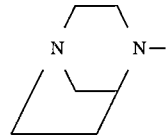

wherein $R_4$ is hydrogen, alkyl of from one to four carbon atoms, or cycloalkyl of from three to six carbon atoms, R' is hydrogen, hydroxyl, alkyl of from one to four carbon atoms, phenyl or phenyl substituted by halogen, alkyl or alkoxy, n is an integer of from 0 to 4, $R_5$ and $R_6$ are each independently hydrogen, lower alkyl or cycloalkyl; X is CH, CF, CCl, CBr, N, CCF$_3$, CNH$_2$, CNO$_2$, CR, or COR' wherein R is lower alkyl and R" is hydrogen or lower alkyl;

$R_3$ is lower straight, branched, or cyclic alkyl of from one to three carbon atoms;

$R_2$ is alkyl of from one to four carbon atoms, vinyl, haloalkyl, hydroxyalkyl of from two to four carbon atoms, cycloalkyl of from three to six carbon atoms, phenyl or phenyl substituted by halogen, alkyl, NH$_2$ or OH;

$R_1$ is hydrogen, alkyl of from one to six carbon atoms, or a cation.

The preferred compounds of this invention are those wherein X is CH, CF, CCl, or N.

Also preferred compounds of the invention are those wherein $R_2$ is cyclopropyl, ethyl, or 2,4-difluorophenyl.

Other preferred compounds of the invention are those wherein $R_3$ is methyl, ethyl, isopropyl, or cyclopropyl.

Other preferred compounds of this invention are those wherein $R_1$ is hydrogen or a pharmaceutically acceptable base salt such as a metal or amine salt.

Other preferred compounds of this invention are those wherein Z is

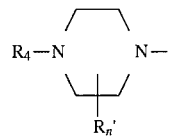

or

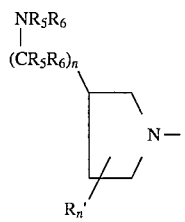

or

wherein $R_4$ is hydrogen or methyl, R' is hydrogen or methyl, n is 0, 1, or 2, $R_5$ and $R_6$ are each independently hydrogen or methyl.

Particularly preferred compounds are those where Z is selected from the group consisting of

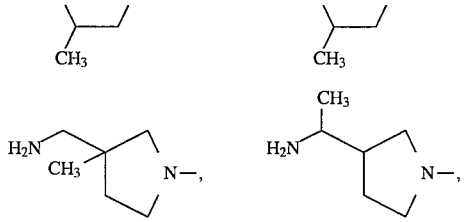

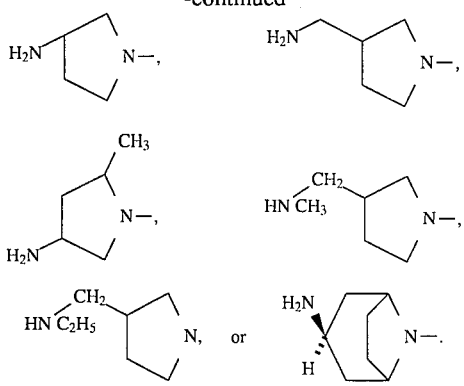

Most preferred compounds include those wherein X is CH, CF, CCl; R₂ is cyclopropyl; R₃ is CH3, Et; R₁ is H; and Z is

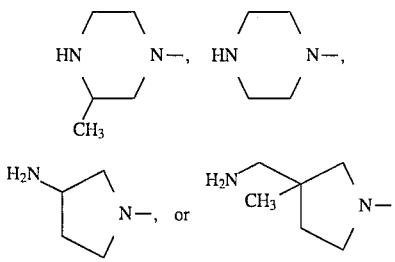

Particularly preferred compounds of the invention are compounds having the names:

1-cyclopropyl-6,8-difluoro-1,4-dihydro-5-methyl-4-oxo-7-(1-piperazinyl) 3-quinolinecarboxylic acid, 7-(3-amino-1-pyrrolidinyl)-1-cyclopropyl-6,8-difluoro-1, 4-dihydro-5-methyl 4-oxo-3-quinolinecarboxylic acid, 1-cyclopropyl-7-[3-[ethylamino)methyl]-1-pyrrolidinyl]-6,8-difluoro-1,4-dihydro 5-methyl-4-oxo-3-quinolinecarboxylic acid, 7-[3-(aminomethyl)-3-methyl-1-pyrrolidinyl]-1-cyclopropyl-6,8-difluoro-1,4-dihydro 5-methyl-4-oxo-3-quinolinecarboxylic acid, 1-cyclopropyl-6,8-difluoro-1,4-dihydro-5-methyl-7-[3-methyl-1-piperazinyl]-4-oxo 3-quinolinecarboxylic acid, 1-cyclopropyl-6-fluoro-1,4-dihydro-5-methyl-4-oxo-7-(1-piperazinyl) 3-quinolinecarboxylic acid, 1-cyclopropyl-6-fluoro-1,4-dihydro-5-methyl-7-(3-methyl-1-piperazinyl)-4-oxo 3-quinolinecarboxylic acid, 7-(3-amino-1-pyrrolidinyl) -1-cyclopropyl-6-fluoro-1,4-dihydro-5-methyl-4-oxo 3-quinolinecarboxylic acid, 6-fluoro-1-(2,4-difluorophenyl)-1,4-dihydro-5-methyl-7-(3-methyl-1-piperazinyl) 4-oxo-3-quinolinecarboxylic acid, 7-(3-amino-1-pyrrolidinyl)-6-fluoro-1-(2,4-difluorophenyl)-1,4-dihydro-5-methyl 4-oxo-3-quinolinecarboxylic acid, 7-[3-(aminomethyl)-3-methyl-1-pyrrolidinyl]-6-fluoro-1-(2,4-difluorophenyl) 1,4-dihydro-5-methyl-4-oxo-3-quinolinecarboxylic acid, 7-[3-(endo-amino)-8-azabicyclo[3.2.1]oct-8-yl]-8-chloro-1-cyclopropyl 6-fluoro-1,4-dihydro-5-methyl-4-oxo-3-quinolinecarboxylic acid, and pharmaceutically acceptable acid addition or base salts thereof.

Other preferred compounds of the invention are compounds having the names:

1-cyclopropyl-6,8-difluoro-1,4-dihydro-5-ethyl-7-[3-methyl-1-piperazinyl]-4-oxo 3-quinolinecarboxylic acid, 7-(3-amino-1-pyrrolidinyl)-1-cyclopropyl-5-ethyl-6,8-difluoro-1,4-dihydro-4-oxo 3-quinolinecarboxylic acid, 7-(3-amino-1-pyrrolidinyl)-1,5-dicyclopropyl-6,8-difluoro-1,4-dihydro-4-oxo 3-quinolinecarboxylic acid, 1-cyclopropyl-7-[3-[(ethylamino)methyl]-1-pyrrolidinyl]- 6-fluoro-1,4-dihydro-5-methyl 4-oxo-3-quinolinecarboxylic acid, 7-[3-(aminomethyl)-3-methyl-1-pyrrolidinyl]-1-cyclopropyl-6-fluoro-1,4-dihydro 5-methyl-4-oxo-3-quinolinecarboxylic acid, 7-(3-amino-1-pyrrolidinyl)-8-chloro-1-cyclo-propyl-6-fluoro-1,4-dihydro-5-methyl 4-oxo-3-quinolinecarboxylic acid, 8-chloro-1-cyclopropyl-7-[3-[(ethylamino)methyl]-1-pyrrolidinyl]-6-fluoro-1,4-dihydro 5-methyl-4-oxo-3-quinolinecarboxylic acid, 8-chloro-1-cyclopropyl-6-fluoro-1,4-dihydro-5-methyl-4-oxo-7-(1-piperazinyl) 3-quinolinecarboxylic acid, 8-chloro-1-cyclopropyl-6-fluoro-1,4-dihydro-5-methyl-7-(3-methyl-1-piperazinyl) 4-oxo-3-quinolinecarboxylic acid, 7-[3-(aminomethyl)-3-methyl-1-pyrrolidinyl]-8-chloco-1-cyclopropyl-6-fluoro 1,4-dihydro-5-methyl-4-oxo-3-quinolinecarboxylic acid, 7-(3-amino-1-pyrrolidinyl)-8-bromo-1-cyclo-propyl-6-fluoro-1,4-dihydro-5-methyl 4-oxo-3-quinolinecarboxylic acid, 8-bromo-1-cyclopropyl-6-fluoro-1,4-dihydro-5-methyl-7-(3-methyl-1-piperazinyl)-4-oxo 3-quinolinecarboxylic acid, 7-[3-(aminomethyl)-3-methyl-1-pyrrolidinyl]-8-bromo-1-cyclopropyl-6-fluoro-1,4-dihydro 5-methyl-4-oxo-3-quinolinecarboxylic acid, 7-(3-amino-1-pyrrolidinyl)-1-cyclopropyl-6-fluoro-1,4-dihydro-8-hydroxy-5-methyl 4-oxo-3-quinolinecarboxylic acid, 1-cyclopropyl-7-[3-[(ethylamino)methyl]-1-pyrrolidinyl] -6-fluoro-1,4-dihydro-8-hydroxy 5-methyl-4-oxo-3-quinolinecarboxylic acid, 1-cyclopropyl-6-fluoro-1,4-dihydro-8-hydroxy-5-methyl-4-oxo-7-(1-piperazinyl) 3-quinolinecarboxylic acid, 7-(3-amino-1-pyrrolidinyl)-1-cyclopropyl-6-fluoro-1,4-dihydro-8-methoxy-5-methyl 4-oxo-3-quinolinecarboxylic acid, 1-cyclopropyl-7-[3-[(ethylamino)methyl]-1-pyrrolidinyl]- 6-fluoro-1,4-dihydro-8-methoxy 5-methyl-4-oxo-3-quinolinecarboxylic acid, 1-cyclopropyl-6-fluoro-1,4-dihydro-8-methoxy-7-(3-methyl-1-piperazinyl)-5-methyl 4-oxo-3-quinolinecarboxylic acid, 7-(3-amino-1-pyrrolidinyl)-1-cyclopropyl-6-fluoro-1,4-dihydro-5-methyl-8-nitro 4-oxo-3-quinolinecarboxylic acid, 1-cyclopropyl-6-fluoro-1,4-dihydro-5-methyl-7-(3-methyl-1-piperazinyl)-8-nitro 4-oxo-3-quinolinecarboxylic acid, 7-[3-(aminomethyl)-3-methyl-1-pyrrolidinyl]-1-cyclopropyl-6-fluoro-1,4-dihydro 5-methyl-8-nitro-4-oxo-3-quinolinecarboxylic acid, 8-amino-7-(3-amino-1-pyrrolidinyl)-1-cyclo-propyl-6-fluoro-1,4-dihydro-5-methyl 4-oxo-3-quinolinecarboxylic acid, 8-amino-1-cyclopropyl-6-fluoro-1,4-dihydro-5-methyl-7-(3-methyl-1-piperazinyl) 4-oxo-3-quinolinecarboxylic acid, 8-amino-7-[3-(aminomethyl)-3-methyl-1-pyrrolidinyl]-1-cyclopropyl-6-fluoro 1,4-dihydro-5-methyl-4-oxo-3-quinolinecarboxylic acid, 7-(3-amino-1-pyrrolidinyl)-1-cyclopropyl-6-fluoro-5-methyl-1,4-dihydro-4-oxo 1,8-naphthyridine-3-carboxylic acid, 1-cyclopropyl-6-fluoro-1,4-dihydro-5-methyl-7-(3-methyl-1-piperazinyl)4-oxo 1,8-naphthyridine-3-carboxylic acid, 1-cyclopropyl-5-ethyl-6-fluoro-1,4-dihydro-4-oxo-7-(1-piperazinyl) 1,8-naphthyridine-3-carboxylic acid, 7-(3-amino-1-pyrrolidinyl)-6,8-difluoro-1-(2,4 -difluorophenyl)-1,4-dihydro 5-methyl-4-oxo-3-quinolinecarboxylic acid, 6,8-difluoro-1-(2,4-difluorophenyl)-1,4-dihydro-5-methyl-7-(3-methyl 1-piperazinyl)-4-oxo-3-quinolinecarboxylic acid, 7-[3-(aminomethyl)-3-methyl-1-pyrrolidinyl]-6,8-difluoro-1-(2,4-difluorophenyl) 1,4-dihydro-5-methyl-4-oxo-3-quinolinecarboxylic acid, 7-(3-amino-1-pyrrolidinyl)-1-ethyl-6,8-difluoro-1,4-dihydro-5-methyl-4-oxo 3-quinolinecarboxylic acid, 1-ethyl-7-[3-[(ethylamino)methyl]-1-pyrrolidinyl]-6,8-difluoro-1,4-dihydro 5-methyl-4-oxo-3-quinolinecarboxylic acid, 7-(3-amino-1-pyrrolidinyl)-6,8-difluoro-1-(2-fluoroethyl)-1,4-dihydro-5-methyl 4-oxo-3-quinolinecarboxylic acid, 6,8-difluoro-1-(2-fluoroethyl)-1,4-dihydro-5-methyl-4-oxo-7-(1-piperazinyl) 3-quinolinecarboxylic acid, 7-(3-amino-1-pyrrolidinyl)-6,8-difluoro-1,4-dihydro-5-methyl-4-oxo 1-vinyl-3-quinolinecarboxylic acid, 6,8-difluoro-1,4-dihydro-5-methyl-4-oxo-7-(1-piperazinyl)-1-vinyl 3-quinolinecarboxylic acid, 6,8-difluoro-1,4-dihydro-5-methyl-7-(3-methyl-1-piperazinyl)-4oxo 1-vinyl-3-quinolinecarboxylic acid, 7-(3-amino-1-pyrrolidinyl)-6-fluoro-1-(2,4-difluorophenyl)-1,4-dihydro 5-methyl-4-oxo-3-quinolinecarboxylic acid, 6-fluoro-1-(2,4-difluorophenyl)-1,4-dihydro-5-methyl-7-(3,5-dimethyl 1-piperazinyl)-4-oxo-3-quinolinecarboxylic acid, 7-(3-amino-1-pyrrolidinyl)-1-ethyl-6-fluoro-1,4-dihydro-5-methyl-4-oxo 3-quinolinecarboxylic acid, 1-ethyl-6-fluoro-1,4-dihydro-5-methyl-4-oxo-7-(1-piperazinyl) 3-quinolinecarboxylic acid, 7-[3-[(ethylamino)methyl]-1-pyrrolidinyl]-6-fluoro-1-(2-fluoroethyl) 1,4-dihydro-5-methyl-4-oxo-3-quinolinecarboxylic acid, 6-fluoro-1-(2-fluoroethyl)-1,4-dihydro-5-methyl-7-(3-methyl-1-piperazinyl) 4-oxo-3-quinolinecarboxylic acid, 7-(3-amino-1-pyrrolidinyl)-6-fluoro-1-(2-fluoroethyl)-1,4-dihydro-5-methyl 4-oxo-3-quinolinecarboxylic acid, 7-(3-amino-1-pyrrolidinyl)-6-fluoro-1,4-dihydro-5-methyl-4oxo-1-vinyl 3-quinolinecarboxylic acid, 6-fluoro-1,4-dihydro-5-methyl-7-(3,5-dimethyl-1-piperazinyl)-4-oxo-1-vinyl 3-quinolinecarboxylic acid, 8-chloro-7-(3-amino-1-pyrrolidinyl)-6-fluoro-1-(2,4-difluorophenyl)-1,4-dihydro 5-methyl-4-oxo-3-quinolinecarboxylic acid, 8-chloro-6-fluoro-1-(2,4-difluorophenyl)-1,4-dihydro-5-methyl-7-(3-methyl 1-piperazinyl)-4-oxo-3-quinolinecarboxylic acid, 7-[3-(aminomethyl)-3-methyl-1-pyrrolidinyl]-8-chloro-6-fluoro-1-(2,4-difluorophenyl) 1,4-dihydro-5-methyl-4-oxo-3-quinolinecarboxylic acid, 8-chloro-6-fluoro-1-(2,4-difluorophenyl)-1,4-dihydro-5-methyl-7-(3,5-dimethyl 1-piperazinyl)-4-oxo-3-quinolinecarboxylic acid, 8-chloro-1-ethyl-6-fluoro-1,4-dihydro-5-methyl-4-oxo-7-piperazinyl 3-quinolinecarboxylic acid, 7-(3-amino-1-pyrrolidinyl)-8-chloro-1-ethyl-6-fluoro-1,4-dihydro-5-methyl 4-oxo-3-quinolinecarboxylic acid, 8-chloro-1-ethyl-7-[3-[(ethylamino)methyl]-1-pyrrolidinyl]-6-fluoro-1,4-dihydro 5-methyl-4-oxo-3-quinolinecarboxylic acid, 7-(3-amino-1-pyrrolidinyl)-8-chloro-6-fluoro-1-(2-fluoroethyl)-1,4-dihydro 5-methyl-4-oxo-3-quinolinecarboxylic acid, 8-chloro-6-fluoro-1-(2-fluoroethyl)-1,4-dihydro-5-methyl-7-(3-methyl-1-piperazinyl) 4-oxo-3-quinolinecarboxylic acid, 7-(3-amino-1-pyrrolidinyl)-8-chloro-6-fluoro-1,4-dihydro-5-methyl-4-oxo 1-vinyl-3-quinolinecarboxylic acid, 8-chloro-6-fluoro-1,4-dihydro-5-methyl-4-oxo-7-(1-piperazinyl)-1-vinyl 3-quinolinecarboxylic acid, 7-(3-amino-1-pyrrolidinyl)-1-cyclopropyl-6-fluoro-1,4-dihydro-5,8-dimethyl-4-oxo 3-quinolinecarboxylic acid, 1-cyclopropyl-6-fluoro-1,4-dihydro-5, 8-dimethyl-4-oxo-7-(1-piperazinyl) 3-quinolinecarboxylic acid, 1-cyclopropyl-6-fluoro-1,4-dihydro-5, 8-dimethyl-7-(3-methyl-1-piperazinyl) 4-oxo-3-quinolinecarboxylic acid, 7-[3-(aminomethyl)-3-methyl-1-pyrrolidinyl]-1-cyclopropyl-6-fluoro-1,4-dihydro 5,8-dimethyl-4-oxo-3-quinolinecarboxylic acid, 1-cyclopropyl-7-[3-[(ethylamino)methyl]-1-pyrrolidinyl]-6-fluoro-1,4-dihydro 5,8-dimethyl-4-oxo-3-quinolinecarboxylic acid, 7-(3-amino-1-pyrrolidinyl)-6-fluoro-1-(2,4-difluorophenyl)-1,4-dihydro 5,8-dimethyl-4-oxo-3-quinolinecarboxylic acid, 6-fluoro-1-(2,4-difluorophenyl)-1,4-dihydro-5,8-dimethyl-7-(3-methyl 1-piperazinyl)-4-oxo-3-quinolinecarboxylic acid, 7-[3-(aminomethyl)-3-methyl-1-pyrrolidinyl]-6-fluoro-1-(2,4-difluorophenyl) 1,4-dihydro-5,8-dimethyl-4-oxo-3-quinolinecarboxylic acid, 7-(3-amino-1-pyrrolidinyl)-1-ethyl-6-fluoro-1,4-dihydro-5,8-dimethyl-4-oxo 3-quinolinecarboxylic acid, 1-ethyl-6-fluoro-1,4-dihydro-5,8-dimethyl-7-(3-methyl-1-piperazinyl)4-oxo 3-quinolinecarboxylic acid, 7-(3-amino-1-pyrrolidinyl)-1-cyclopropyl-6-fluoro-8-trifluoromethyl-1,4-dihydro 5-methyl-4-oxo-3-quinolinecarboxylic acid, 1-cyclopropyl-6-fluoro-8-trifluoromethyl-1,4-dihydro-5-methyl-4-oxo-7-(1-piperazinyl) 3-quinolinecarboxylic acid, 1-cyclopropyl-6-fluoro-8-trifluoromethyl-1,4-dihydro-5-methyl-7-(3-methyl-1-piperazinyl) 4-oxo-3-quinolinecarboxylic acid, 7-[3-(aminomethyl)-3-methyl-1-pyrrolidinyl]-1-cyclopropyl-6-fluoro-8-trifluoromethyl 1,4-dihydro-5-methyl-4-oxo-3-quinolinecarboxylic acid, 1-cyclopropyl-7-[3-[(ethylamino)methyl]-1-pyrrolidinyl]-6-fluoro-8-trifluoromethyl 1,4-dihydro-5-methyl-4-oxo-3-quinolinecarboxylic acid, 7-(3-amino-1-pyrrolidinyl)-6-fluoro-1-(2,4-difluorophenyl)-8-trifluoromethyl 1,4-dihydro-5-methyl-4-oxo-3-quinolinecarboxylic acid, 6-fluoro-1-(2,4-difluorophenyl)-8-trifluoromethyl-1,4-dihydro-5-methyl 7-(3-methyl-1-piperazinyl)-4-oxo-3-quinolinecarboxylic acid, 7-[3-(aminomethyl)-3-methyl-1-pyrrolidinyl]-6-fluoro-1-(2,4-difluorophenyl) 8-trifluoromethyl-1,4-dihydro-5-methyl-4-oxo-3-quinolinecarboxylic acid, 7-(3-amino-1-pyrrolidinyl)-1-ethyl-6-fluoro-8-trifluoromethyl-1,4-dihydro 5-methyl-4-oxo-3-quinolinecarboxylic acid, 1-ethyl-6-fluoro-8-trifluoromethyl-1,4-dihydro-5-methyl-7-(3-methyl-1-piperazinyl) 4-oxo-3-quinolinecarboxylic acid, 1-ethyl-6,8-difluoro-1,4-dihydro-5-methyl-4-oxo-7-(1-piperazinyl) 3-quinolinecarboxylic acid, 6,8-difluoro-1-(2,4-difluorophenyl)-1,4-dihydro-5-methyl-4-oxo-7-(1-piperazinyl) 3-quinolinecarboxylic acid, 6,8-difluoro-1-(2,4-difluorophenyl)-1,4-dihydro-5-methyl-7-(3,5-dimethyl-1-piperazinyl) 4-oxo-3-quinolinecarboxylic acid, 6-fluoro-1-(2,4-difluorophenyl)-1,4-dihydro-5-methyl-4-oxo-7-(1-piperazinyl) 3-quinolinecarboxylic acid, and 7-[3-(ethylamino)methyl-1-pyrrolidinyl]-6-fluoro-1-(2,4-difluorophenyl)-1,4-dihydro 5-methyl-4-oxo-3-quinolinecarboxylic acid.

Other preferred compounds of the invention are:

7-(3-amino-1-pyrrolidinyl)-1-(2,4-difluorophenyl)-6-fluoro-1,4-dihydro-5-methyl 4-oxo-1,8-naphthyridine-3-carboxylic acid, 3R,1'S-7-[3-(1-amino-ethyl)-1-pyrrolidinyl]-1-(2,4-difluorophenyl)-6-fluoro 1,4-dihydro-5-methyl-4-oxo-1, 8-naphthyridine carboxylic acid, 3R, 1'S-7-[3-(1-(N-methylamino)ethyl)-1-pyrrolidinyl]-1-(2,4-difluorophenyl) 6-fluoro-1,4-dihydro-5-methyl-4-oxo-1,8-naphthyridine-3-carboxylic acid, 3R-7-[3-(1-amino-1-methylethylpyrrolidin-1-yl]-1-(2,4-difluorophenyl)-6-fluoro 1,4-dihydro-5-methyl-4-oxo-1,8-naphthyridine-3-carboxylic acid, 3S-7-[3-amino-1-pyrrolidinyl]-1-(2,4-difluorophenyl)-6-fluoro-1,4-dihydro 5-methyl-4-oxo-1,8-naphthyridine-3-carboxylic acid, 7-[(3-N-ethylaminomethyl)pyrrolidin-1-yl]-1-cyclopropyl-6-fluoro-1,4-dihydro-5-methyl 4-oxo-1,8-naphthyridine-3-carboxylic acid, and 7-(3-aminomethylpyrrolidin-1-yl)-1-cyclopropyl-6-fluoro-1,4-dihydro-5-methyl 4-oxo-1,8-naphthyridine carboxylic acid.

The invention further includes certain novel intermediate compounds having the names:

1-cyclopropyl-6,7,8-trifluoro-1,4-dihydro-5-methyl-4-oxo-3-quinolinecarboxylic acid ethyl ester, 2,3,4,5-tetrafluoro-6-methylbenzoic acid, 2,3,4,5-tetrafluoro-6-methylbenzoyl chloride, ethyl 3-(2,3,4,5-tetrafluoro-6-methylphenyl)-β-oxo-propanoate, ethyl 2-(2,3,4,5-tetrafluoro-6-methylbenzoyl) -3-ethoxyacrylate, 2-(2,4,5-trifluoro-3-trimethylsilylphenyl)-4,4-dimethyl-2-oxozoline, ethyl 2-(2,3,4,5-tetrafluoro-6-methylbenzoyl)-3-cyclopropylaminoacrylate, 2-(2,4,5-trifluoro-6-methyl-3-trimethylsilylphenyl-phenyl)-4,4-dimethyl-2-oxazoline, 2-(2,4,5-trifluoro-6-methylphenyl)-4,4-dimethyl-2-oxazoline, 2-(3-chloro-2,4,5-trifluoro-6-methylphenyl)-4,4-dimethyl-2-oxazoline, 2-(3-bromo-2,4,5-trifluoro-6-methylphenyl)-4,4-dimethyl-2-oxazoline, 2-(2,4,5-trifluoro-3-hydroxy-6-methylphenyl)-4,4-dimethyl-2-oxazoline, 2-(2,4,5-trifluoro-6-methyl-3-nitrophenyl)-4,4-dimethyl-2-oxazoline, 2-(2,4,5-trifluoro-3,6-dimethylphenyl)-4,4-dimethyl-2-oxazoline, 2-[2,4,5-trifluoro-3-(trifluoromethyl)-6-methylphenyl]-4, 4-dimethyl-2-oxazoline, 2,6-dichloro-5-fluoro-4-methyl-3-pyridinecarboxylic acid, 3-chloro-2,4,5-trifluoro-6-methylbenzoic acid, 3-bromo-2,4, 5-trifluoro-6-methylbenzoic acid, 2,4,5-trifluoro-6-methyl-3-nitrobenzoic acid, and 2,4, 5-trifluoro-3, 6-dimethylbenzoic acid.

Another aspect of the instant invention is the following process for preparing compounds of Formula I

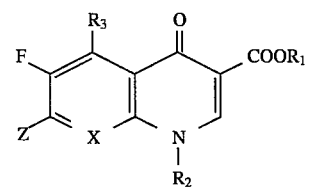

Formula I wherein $R_1$, $R_2$, $R_3$, $R_4$, $R_5$, $R_6$, Z, n, R' and X are as defined above which comprises reacting a compound of Formula II

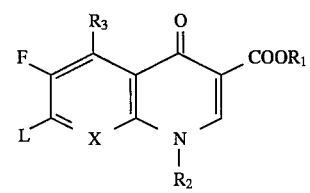

Formula II with an amine corresponding to the group Z wherein all of the above terms are as defined above in Formula I and L is a leaving group which may preferably be fluorine or chlorine.

Yet another aspect of the instant invention is process for preparing compounds of formula

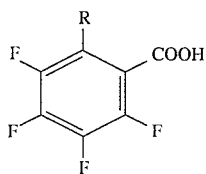

wherein R is alkyl which comprises reacting a pentafluorooxazoline with alkyl lithium producing a compound of formula

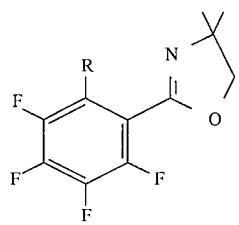

followed by acidic hydrolysis.

Yet another aspect of the present invention is a process for preparing compounds of formula

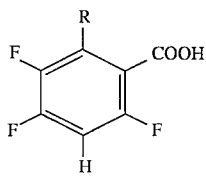

wherein R is alkyl which comprises (a) reacting a compound of formula

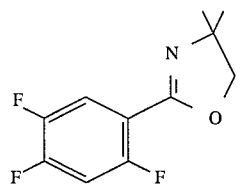

with a base and trimethylsilyl chloride producing a compound of formula

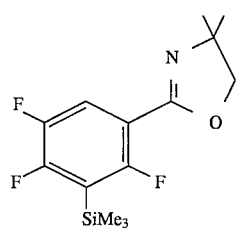

(b) reacting that compound with a base and an alkyl halide producing a compound of formula

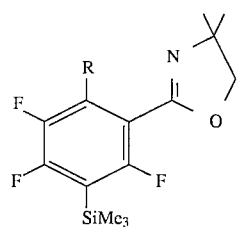

(c) removing the SiMe$_3$ and (d) hydrolyzing the resulting compound.

Yet another aspect of the present invention is a process for preparing naphthyridines of Formula I by (a) reacting a compound of formula

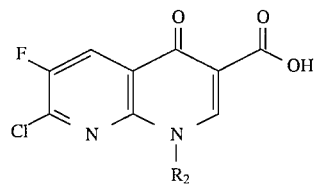

with oxalyl chloride and dimethylformamide and quenching with alcohol to produce the corresponding ester

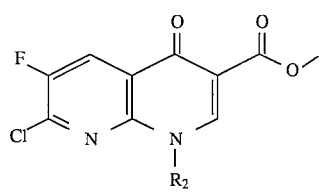

(b) reducing the double bond to produce a compound of formula

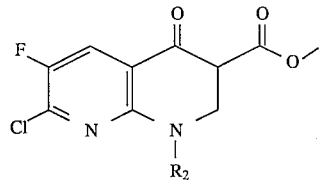

(c) treating the compound from step (b) with a base, then methyl iodide to produce the alkylated compound

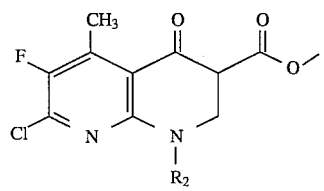

(d) reintroducing the double bond and reacting the resulting naphthyridine with the desired amine by known means.

The invention also includes a pharmaceutical composition which comprises an antibacterially effective amount of a compound having structural Formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DETAILED DESCRIPTION

The compound of the invention having the structural Formula I may be readily prepared by treating a corresponding compound having the Formula II above with the desired cyclic amine as defined by Z. For purposes of this reaction, the alkylamine substituent of Z may, if desired, be protected by a group which renders it substantially inert to the reaction conditions. Thus, for example, protecting groups such as the following may be utilized:

carboxylic acyl groups such as formyl, acetyl, trifluoroacetyl;

alkoxycarbonyl groups such as ethoxycarbonyl, t-butoxycarbonyl, β,β,β-trichloroethoxycarbonyl, β-iodoethoxycarbonyl;

aryloxycarbonyl groups such as benzyloxycarbonyl, p-methoxybenzyloxycarbonyl, phenoxycarbonyl;

silyl groups such as trimethylsilyl; and groups such as trityl, tetrahydropyranyl, vinyloxycarbonyl, o-nitrophenylsulfenyl, diphenylphosphinyl, p-toluenesulfonyl, and benzyl may all be utilized.

The protecting group may be removed after the reaction between a compound as defined by Formula II and Z if desired, by procedures known to those skilled in the art. For example, the ethoxycarbonyl group may be removed by acid or base hydrolysis and the trityl group may be removed by hydrogenolysis.

The reaction between the compound Formula II and a suitably protected compound as defined by Z may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of Formula VI may be utilized as the acid acceptor.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group may be accomplished either before or after isolating the product, I. Alternatively, the protecting group need not be removed.

The compounds of the invention of Z are either known compounds or they may be prepared from known starting materials by standard procedures or by variations thereof. For example, 3-pyrrolidinemethanamines having the formula D

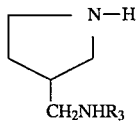

may be readily prepared from the known starting material methyl 5-oxo-1-(phenylmethyl)-3-pyrrolidine-carboxylate, A, [J. Org. Chem., 26, 1519 (1961)] by the following reaction sequence.

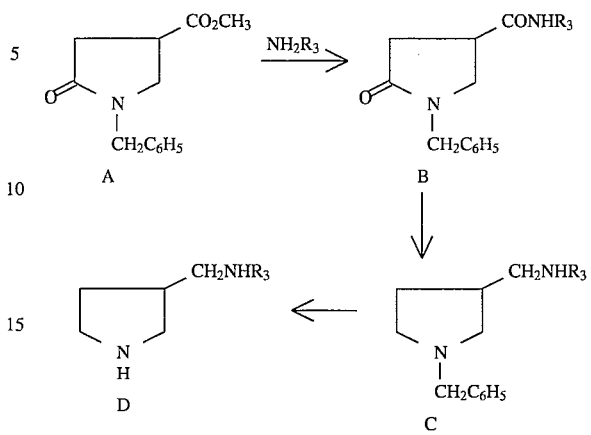

The compound wherein $R_3$ is hydrogen, namely 3-pyrrolidinemethanamine, has been reported in J. Org. Chem., 26, 4955 (1961).

Thus Compound A may be converted to the corresponding amide B by treatment with $R_3NH_2$; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when R=H in C, the primary amine function may be protected with a group $R_4$ as defined, hereinabove. For example, the primary amine function may be acylated with an acyl halide such as acetyl chloride by well known procedures. The primary amine function of C may also be converted to a carbamate ester such as the ethyl ester by treatment with ethyl chloroformate in the presence of a strong base such as 1,8-diazabicyclo[5.4.0]undec-7-ene in a convenient solvent such as methylene chloride. The benzyl group may next be removed, for example as described above for Compound C, thereby producing Compound D where R is —$CO_2Et$, which after conversion to a compound of Z may be reacted with a compound having the Formula II to thereby produce a corresponding compound having the Formula I. The —$CO_2Et$ group may be removed by standard procedures.

The syntheses of the starting compounds represented by Formula II are illustrated in the following schemes.

Scheme 1 below illustrates the formation of 1-cyclopropyl-6,7,8-trifluoro-1,4-dihydro-5-alkyl-4-oxo-3-quinolinecarboxylic acid.

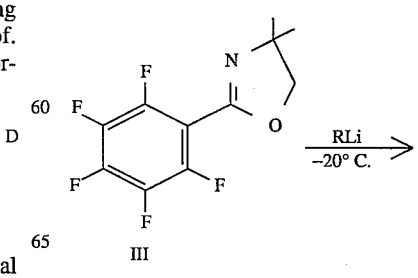

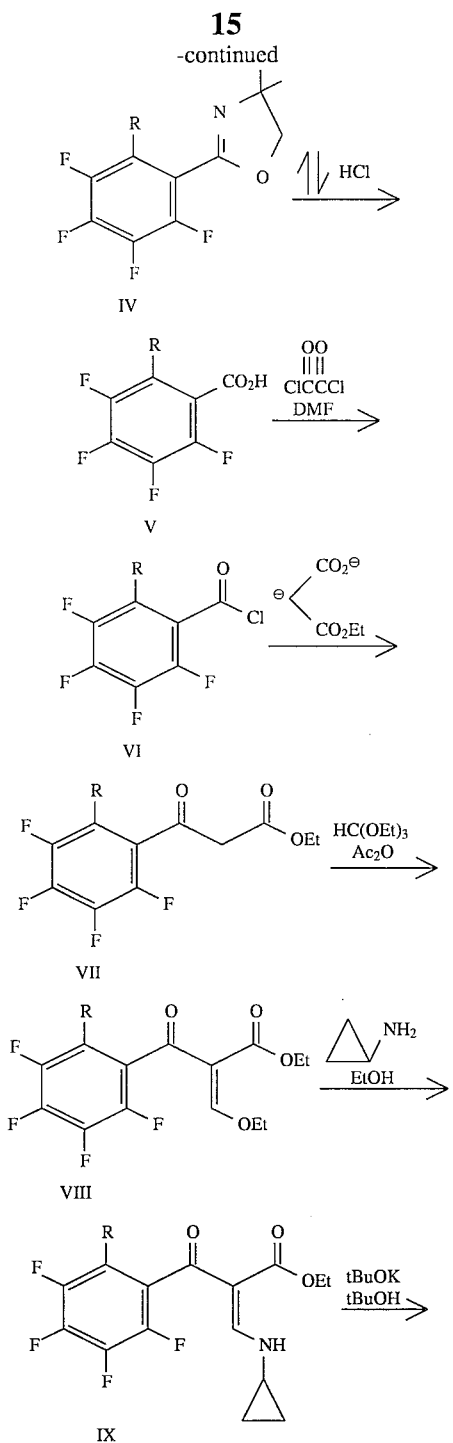

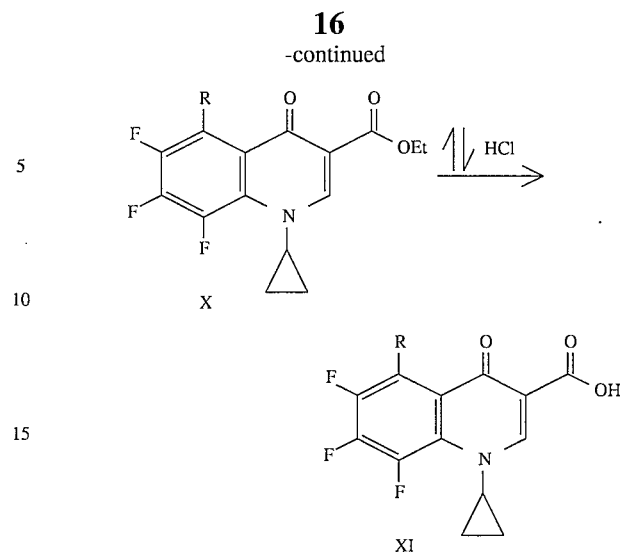

In Scheme 1 above the 2-pentafluorophenyl-4,4-dimethyl-2-oxazoline III is reacted with alkyl lithium at −20° C. to +25° C. to give the 2-(2,3,4,5-tetrafluoro-6-alkylphenyl)-4,4-dimethyl-2-oxazoline IV which is hydrolyzed under acidic conditions (preferably refluxing dilute hydrochloric acid) to give the corresponding benzoic acid V. Compound V is reacted with oxalyl chloride and the product condensed with the dianion of monoethyl malonate (prepared from monoethyl malonic acid and n-butyl lithium in THF) to produce ketoester VII. This ketoester is treated with triethyl orthoformate in acetic anhydride to form adduct VIII. Reaction of compound VIII with cyclopropylamine in t-butanol or ether gives enamine IX; other primary amines can be used in this reaction, such as aliphatic amines (ethylamine, etc) and aromatic amines (p-fluoroaniline, 2,4-difluoroaniline, etc). The enamine is reacted with potassium t-butoxide in dry t-butanol to form the desired cyclized compound X, which can be hydrolyzed in refluxing acid to give Compound XI.

Scheme 2 below illustrates syntheses of 5-alkyl, 8-X quinolines (X≠F).

Scheme 2

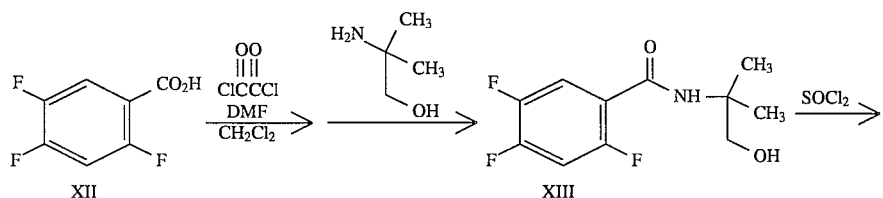

-continued
Scheme 2
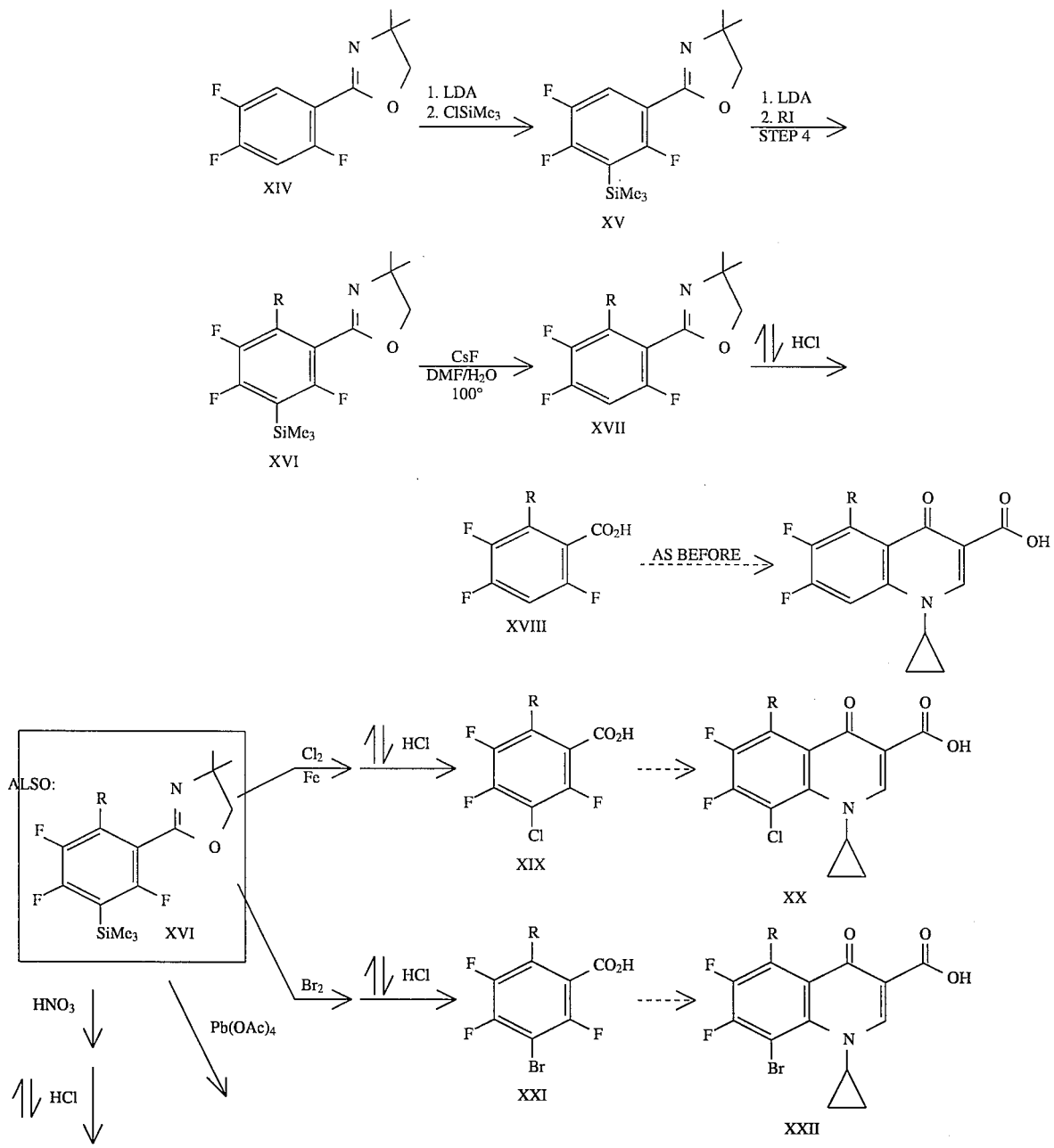

-continued
Scheme 2

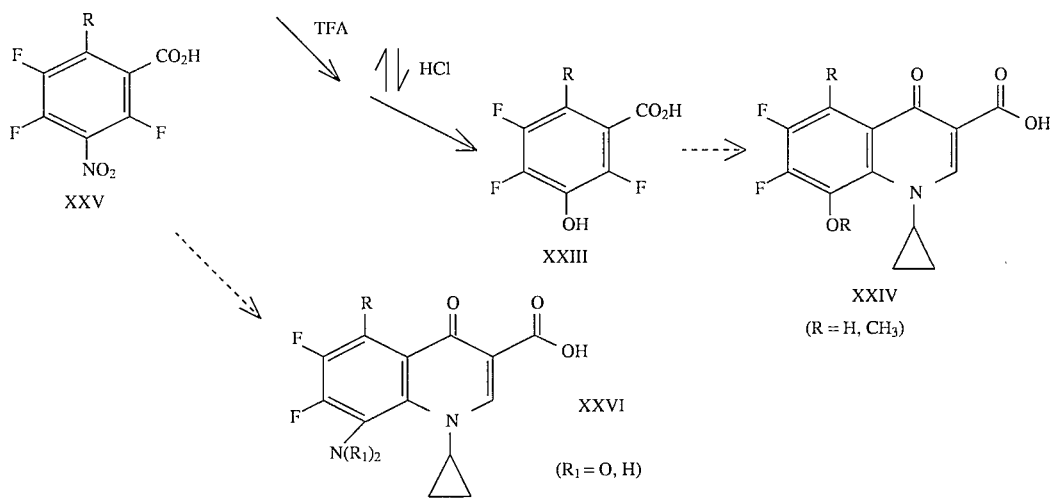

In Scheme 2 above the acid XII is converted to its acid chloride via reaction with oxalyl chloride, and the acid chloride is treated with 2-amino-2-methyl-1-propanol to give N-(2-hydroxy-1,1-dimethyl-ethyl)-2,4,5-trifluorocarboxamide (Compound XIII). This amide is cyclized to the crucial intermediate oxazoline XIV by reaction with thionyl chloride in chloroform. Compound XIV is then treated with a base, preferably lithium diisopropylamide, in THF or ether at −78° C. and quenched with trimethylsilyl chloride to produce silylated oxazoline XV. Compound XV is treated with base (again, preferably lithium diisopropylamide) in THF or ether at 0°–20° C. and then quenched with an alkyl iodide to give, upon work-up, the alkylated intermediate XVI. Removal of the trimethylsilyl group is accomplished by treatment with cesium fluoride in wet DMF; the resulting compound XVII is hydrolyzed to the corresponding benzoic acid XVIII in refluxing dilute hydrochloric acid. This benzoic acid is elaborated into 1-cyclo-propyl-6,7-difluoro-1,4-dihydro 5-alkyl-4-oxo-3-quinolinecarboxylic acid using the methodology previously described in Scheme 1.

Alternatively, silylated intermediate XVI can be transformed into a variety of 3-substituted compounds via ipso attack on the trimethylsilyl group. For example, Compound XVI is reacted with chlorine in the presence of iron powder and then hydrolyzed in dilute refluxing acid to give 3-chloro-2,4,5-trifluoro-6-alkylbenzoic acid XIX; this acid is elaborated as before to give quinoline XX. Similarly, oxazoline XVI is treated with N-bromosuccinimide in chloroform (or with pyridinium bromide perbromide in dichloromethane) to give the analogous 3-bromo oxazoline which is hydrolyzed and carried on to give Compound XXII. Reaction of intermediate XVI with lead tetraacetate and trifluoroacetic acid, followed by acid hydrolysis, gives 2,4,5-trifluoro-3-hydroxy-6-alkylbenzoic acid (XXIII); the phenol can be converted to the methyl ether via reaction with methyl iodide and potassium carbonate in acetone. This 2,4,5-trifluoro-3-methoxy- 6-alkylbenzoic acid is carried on to the 8-methoxy quinoline XXIV (where R=CH₃); further treatment with HBr cleaves the methyl ether to give the corresponding 8-hydroxy quinoline XXIV (where R=H). Finally, nitration of silylated compound XVI with nitric acid in sulfuric acid and hydrolysis of the consequent compound yields nitro acid XXV, which is further elaborated to afford 1-cyclopropyl-6,7-difluoro-1,4-dihydro-5-alkyl-8-nitro-4-oxo 3-quinolinecarboxylic acid XXVI (where R₁=O).

Reduction of the nitro group to the amino group can be accomplished using Raney nickel to yield quinoline XXVI (where R₁=H).

Scheme 2A below outlines an alternative route to the 5-alkyl, 8-chloro quinolones.

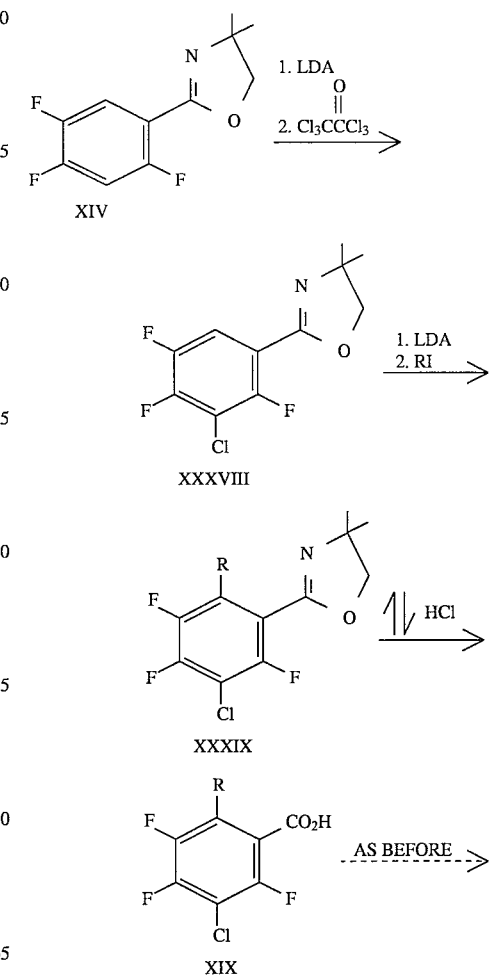

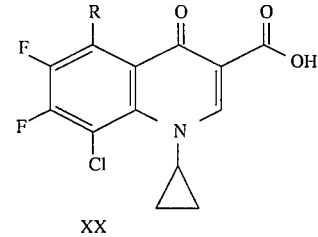

XX

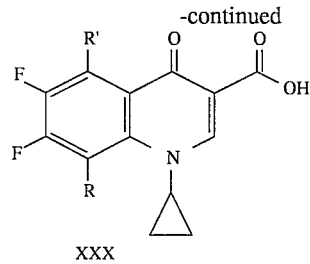

where R or/and R' = CH₃, Et, propyl.

XXX

In Scheme 2A above the oxazoline XIV is treated with a base, preferably lithium diisopropylamide, in THF at −78° C. and quenched with hexachloro acetone to produce the chloro oxazoline XXXVIII. Compound XXXVIII is treated again with a base, preferably lithium diisopropylamide, in THF at 0° C. and quenched with an alkyl iodide to give, upon work-up, the intermediate XXXIX. Hydrolysis of the oxazoline moiety in refluxing dilute hydrochloric acid gives benzoic acid XIX. This acid is elaborated into 8-chloro-1-cyclopropyl-6,7-difluoro-1,4-dihydro-5-alkyl-4-oxo 3-quinolinecarboxylic acid (XX).

Scheme 3 below illustrates synthesis of 5,8-dialkyl quinolines.

In Scheme 3 above oxazoline XIV (prepared in Scheme 2) is treated with a base, preferably lithium diisopropylamide, in THF at −78° C. and is quenched with an alkyl halide (such as methyl iodide, ethyl iodide, etc) to give Compound XXVII, where R=alkyl. Treatment with additional base (preferably lithium diisopropylamide) in ether at 0° C. followed by addition of an alkyl halide affords dialkyl oxazolines such as XXVIII. The intermediates are hydrolyzed and carried on as before to give 5,8-dialkyl-1-cyclopropyl-6,7-difluoro-1,4-dihydro-4-oxo 3-quinolinecarboxylic acids XXX.

Scheme 4 below illustrates syntheses of 5-alkyl naphthyridines.

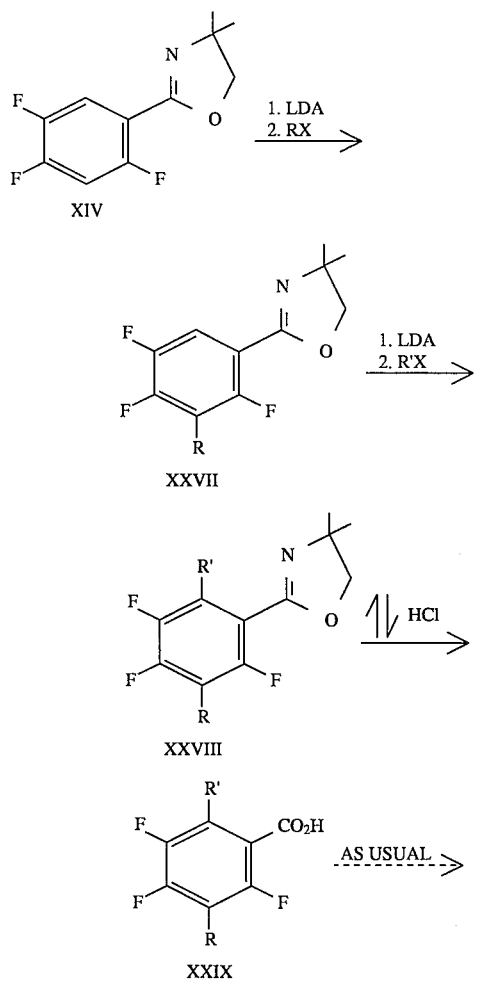

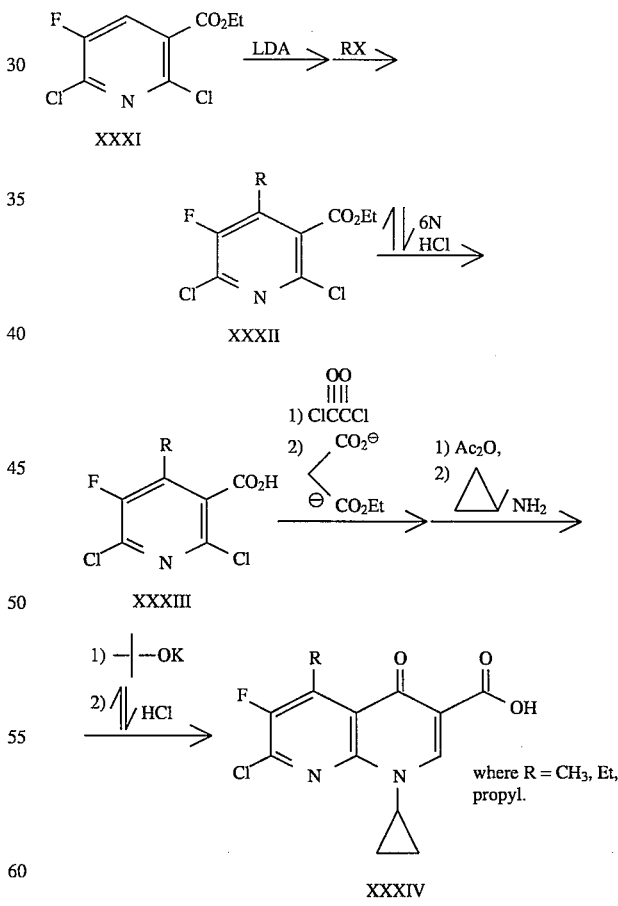

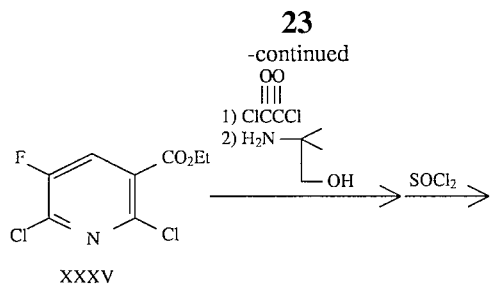
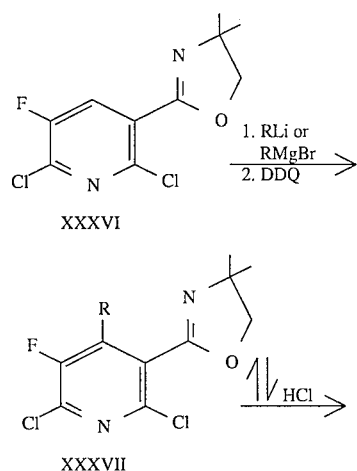
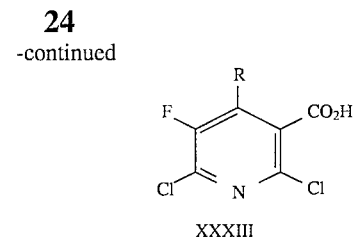

In Scheme 4 above pyridine ester XXXI (Chem. Pharm. Bull. 35, 2280 (1987) is reacted with a base such as lithium diisopropylamide in THF at low temperature followed by an alkyl halide such as ethyl iodide or methyl iodide; hydrolysis of the ester in dilute acid affords compound XXXIII.

Alternatively, ester XXXI can be hydrolyzed in dilute acid to give pyridine acid XXXV which is, in turn, converted to the corresponding oxazoline in the usual manner (see Scheme 2). This oxazoline (Compound XXXVI) is reacted with an alkyl lithium (such as methyl lithium), then rearomatized with DDQ or chloranil. This sequence of reactions gives the alkyl-substituted pyridine XXXVII, which yields, upon acid hydrolysis, the necessary intermediate XXXIII.

Compound XXXIII can be elaborated to the 5-alkyl-7-chloro-1-cyclopropyl-6-fluoro-1,4-dihydro-4-oxo 1,8-naphthyridine-3-carboxylic acid in the usual manner.

Scheme 5

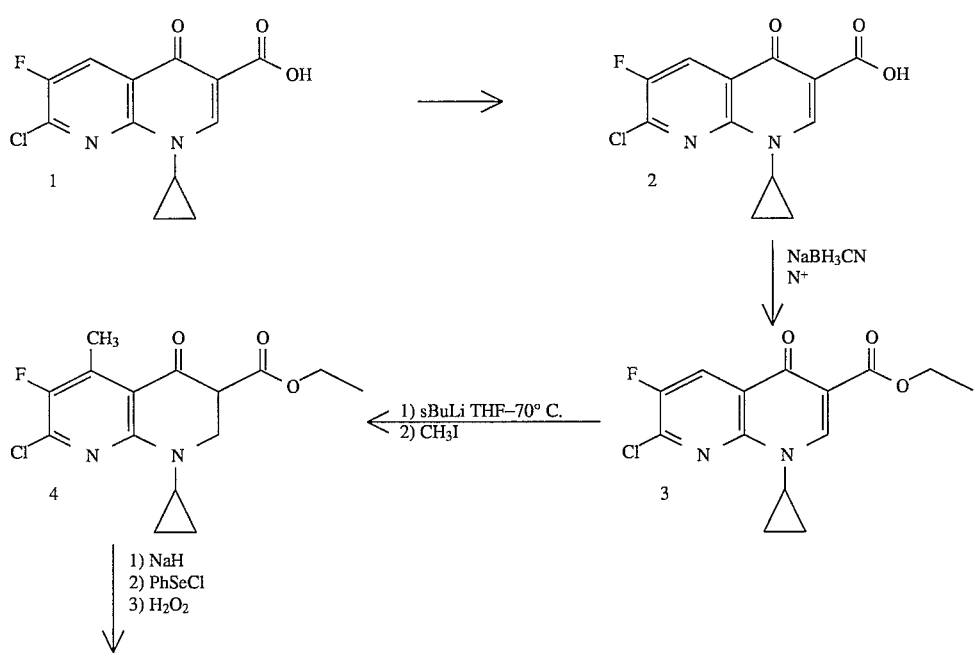

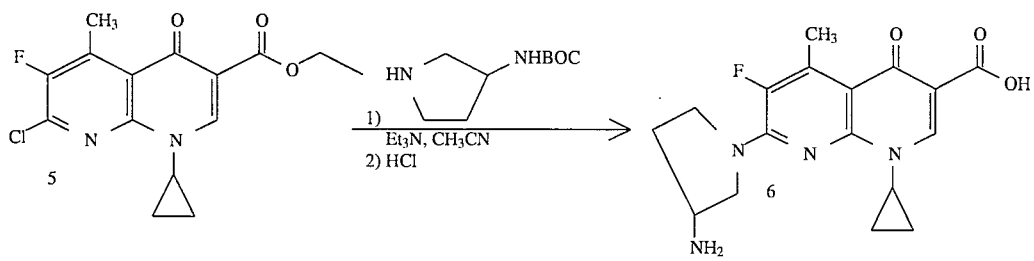

Also prepared by this method:

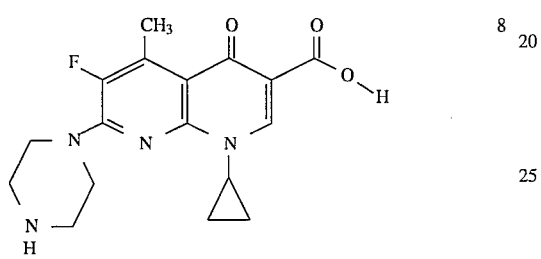

In Scheme 5 above, the known naphthyridine acid 1 (U.S. Pat. No. 4,663,457, 1987) is reacted with oxalyl chloride and DMF and then quenched with absolute ethanol to give ester 2. Reduction of the double bond is accomplished with sodium cyanoborohydride to afford compound 3, which is then treated with sec-butyllithium at −78° C. This dianion is treated with methyl iodide to give the alkylated intermediate 4. The double bond is reintroduced in a series of steps: first, treatment with sodium hydride, followed by addition of phenylselanyl chloride and oxidation with hydrogen peroxide. The final ester 5 can then be reacted with a variety of amines in the usual fashion, which are then hydrolyzed to the acids.

Scheme 6 outlines a synthesis of 5-alkyl, 8-trifluoromethyl derivatives.

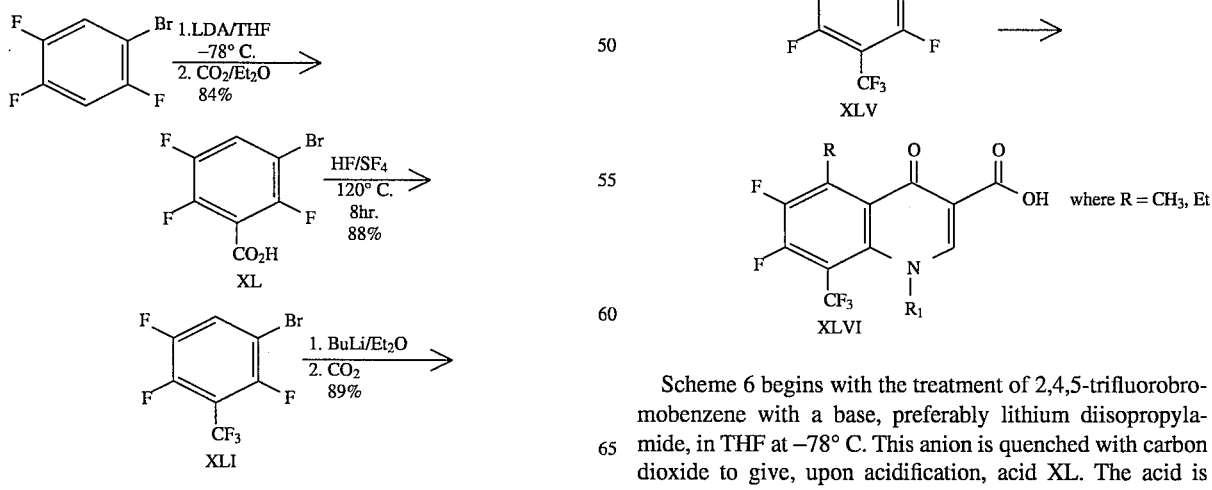

Scheme 6 begins with the treatment of 2,4,5-trifluorobromobenzene with a base, preferably lithium diisopropylamide, in THF at −78° C. This anion is quenched with carbon dioxide to give, upon acidification, acid XL. The acid is reacted with HF/SF$_4$ at 120° C. to afford the trifluoromethyl derivative XLI. The requisite acid functionality is introduced via halogen-metal exchange (preferably with butyl lithium in ether at −78° C.) followed by carbon dioxide quench and acidification. Compound XLII is then treated with oxalyl chloride to form the acid chloride and added to 2-amino-2-methyl-1-propanol in chloroform at 0° C. to produce hydroxy amide XLIII. Cyclization to the key intermediate oxazoline XLIX is accomplished in the usual manner—that is, treatment with thionyl chloride followed by sodium hydride. Deprotonation of XLIV by lithium diisopropylamide at −78° C. and reaction of the anion with an alkyl iodide yields the fully substituted oxazoline XLV which can be elaborated into the target quinolone XLVI using the previously established methodology.

Scheme 7

Scheme 7 outlines an additional synthesis of 5-alkyl 1-substituted-1,8-naphthyridinecarboxylic acid derivatives.

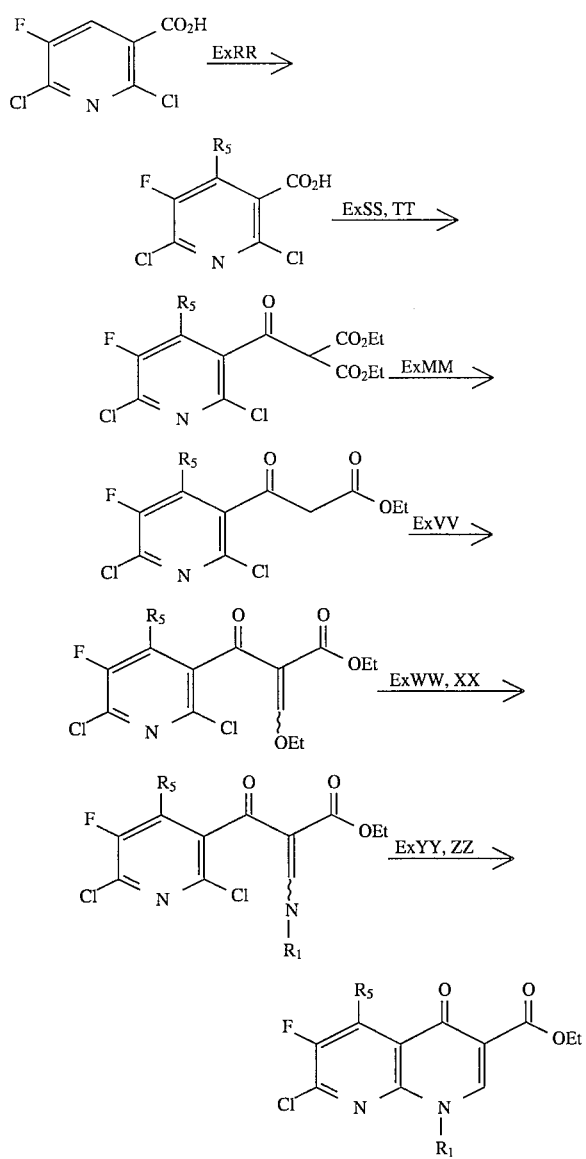

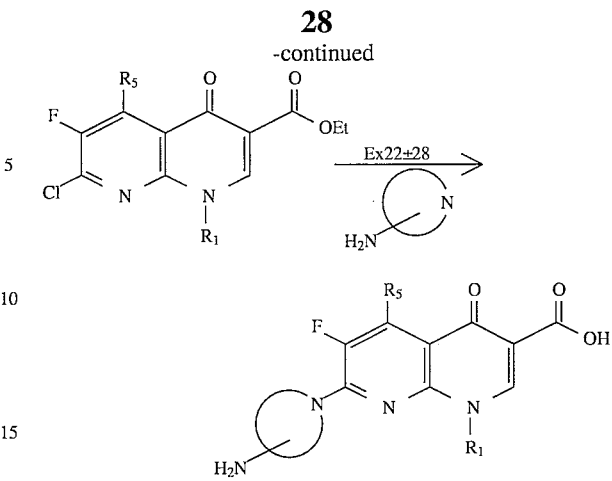

The introduction of the methyl group on the 1,8-naphthyridine substrate was accomplished by the formation of the di-anion of 2,6-dichloro-5-fluoronicotinic acid, preferably with lithium diisopropylamide in THF between −70° C. and −50° C. The di-anion was quenched with iodomethane and the target acid 2, 6-dichloro-5-fluoro-4-methylnicotinic acid is obtained after acidification. The remaining portion of the naphthyridine nucleus was elaborated using previously developed methodology.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compound of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about six carbon atoms. Representative of such groups are methyl, ethyl, propyl, isopropyl, and the like.

The cycloalkyl groups contemplated by the invention comprise those having three to six carbon atoms such as cyclopropyl, cyclobutyl, cyclopentyl, and cyclohexyl.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2-propyl, γ-iodobutyl, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional asymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compounds of the invention display antibacterial activity when tested by the microtitration dilution method as described in Heifetz, et al, Antimicr. Agents & Chemoth., 6, 124 (1974), which is incorporated herein by reference. By use of this method, the followed minimum inhibitory concentration values (MICs in µg/mL) were obtained for representative compounds of the invention.

IN VITRO ANTIBACTERIAL ACTIVITY
Minimal Inhibitory Concentration
MIC (μg/mL)

| Organism | Compound Ex. 1 | Compound Ex. 2 | Compound Ex. 3 | Compound Ex. 4 | Compound Ex. 5 | Compound Ex. 6 |
|---|---|---|---|---|---|---|
| *Enterobacter cloacae* MA 2646 | 0.025 | 0.006 | 0.1 | 0.05 | 0.025 | 0.013 |
| *Escherichia coli* Vogel | 0.025 | 0.006 | 0.05 | 0.05 | 0.05 | 0.013 |
| *Klebsiella pneumoniae* MGH-2 | 0.025 | 0.013 | 0.1 | 0.1 | 0.05 | 0.05 |
| *Providencia rettgeri* M 1771 | 0.05 | 0.025 | 0.2 | 0.2 | 0.10 | 0.10 |
| *Pseudomonas aeruginosa* UI-18 | 0.2 | 0.4 | 0.8 | 0.8 | 0.4 | 0.20 |
| *Staphylococcus aureus* H 228 | 0.025 | 0.013 | 0.013 | 0.006 | 0.025 | 0.10 |
| *Staphylococcus aureus* UC-76 | 0.025 | 0.003 | 0.003 | 0.003 | 0.013 | 0.025 |
| *Streptococcus faecalis* MGH-2 | 0.05 | 0.025 | 0.025 | 0.025 | 0.10 | 0.05 |
| *Streptococcus pneumoniae* SV-1 | 0.025 | 0.003 | 0.003 | 0.003 | 0.025 | 0.05 |
| *Streptococcus pyogenes* C-203 | 0.05 | 0.013 | 0.006 | 0.003 | 0.006 | 0.10 |

| Organisms | Compound Ex. 7 | Compound Ex. 8 | Compound Ex. 9 | Compound Ex. 10 | Compound Ex. 11 | Compound Ex. 12 |
|---|---|---|---|---|---|---|
| *Enterobacter cloacae* MA 2646 | 0.025 | 0.05 | 0.10 | 0.05 | 0.05 | 0.05 |
| *Escherichia coli* Vogel | 0.013 | 0.025 | 0.10 | 0.025 | 0.013 | 0.05 |
| *Klebsiella pneumoniae* MGH-2 | 0.05 | 0.10 | 0.40 | 0.10 | 0.05 | 0.20 |
| *Proteus rettgeri* M 1771 | 0.20 | 0.10 | 0.80 | 0.20 | 0.05 | 0.40 |
| *Pseudomonas aeruginosa* UI-18 | 0.80 | 0.40 | 1.6 | 0.20 | 0.20 | 1.6 |
| *Staphylococcus aureus* H 228 | 0.10 | 0.10 | 0.025 | 0.05 | 0.025 | 0.8 |
| *Staphylococcus aureus* UC-76 | 0.025 | 0.025 | 0.006 | 0.025 | 0.013 | 0.2 |
| *Streptococcus faecalis* MGH-2 | 0.10 | 0.40 | 0.10 | 0.20 | 0.05 | 3.1 |
| *Streptococcus pneumoniae* SV-1 | 0.025 | 0.013 | 0.006 | 0.10 | 0.025 | 6.3 |
| *Streptococcus pyogenes* C-203 | 0.05 | 0.025 | 0.013 | 0.20 | 0.05 | 12.5 |

| Organisms | Compound Ex. 13 | Compound Ex. 14 | Compound Ex. 14a | Compound Ex. 15 | Compound Ex. 17 | Compound Ex. 17a |
|---|---|---|---|---|---|---|
| *Enterobacter cloacae* MA 2646 | 0.05 | 0.1 | 0.4 | 0.025 | 0.05 | 0.2 |
| *Escherichia coli* Vogel | 0.05 | 0.05 | 0.4 | 0.025 | 0.05 | 0.1 |
| *Klebsiella pneumoniae* MGH-2 | 0.2 | 0.4 | 1.6 | 0.1 | 0.1 | 0.4 |
| *Proteus rettgeri* M 1771 | 0.4 | 0.4 | 3.1 | 0.2 | 0.2 | 0.8 |
| *Pseudomonas aeruginosa* UI-18 | 1.6 | 0.8 | 3.1 | 0.8 | 0.8 | 1.6 |
| *Staphylococcus aureus* H 228 | 0.4 | 0.2 | 0.4 | 0.05 | 0.1 | 0.1 |
| *Staphylococcus aureus* UC-76 | 0.1 | 0.05 | 0.2 | 0.025 | 0.025 | 0.025 |
| *Streptococcus faecalis* MGH-2 | 0.8 | 0.4 | 1.6 | 0.2 | 0.2 | 0.4 |
| *Streptococcus pneumoniae* SV-1 | 1.6 | 0.4 | 0.8 | 0.1 | 0.05 | 0.05 |
| *Streptococcus pyogenes* C-203 | 3.1 | 0.4 | 1.6 | 0.1 | 0.1 | 0.1 |

| Organisms | Compound Ex. 17b | Compound Ex. 17c | Compound Ex. 17e | Compound Ex. 18 | Compound Ex. 19 | Compound Ex. 22 | Compound Ex. 23 |
|---|---|---|---|---|---|---|---|
| *Enterobacter cloacae* MA 2646 | 0.4 | 0.05 | 0.4 | 0.013 | 0.025 | 0.05 | 0.2 |
| *Escherichia coli* Vogel | 0.2 | 0.05 | 0.4 | 0.013 | 0.013 | 0.05 | 0.1 |
| *Klebsiella pneumoniae* MGH-2 | 0.8 | 0.1 | 0.8 | 0.025 | 0.05 | 0.05 | 0.1 |
| *Proteus rettgeri* M 1771 | 1.6 | 0.2 | 0.8 | 0.1 | 0.2 | 0.1 | 0.2 |
| *Pseudomonas aeruginosa* UI-18 | 1.6 | 0.8 | 3.1 | 0.2 | 0.4 | 0.2 | 0.2 |
| *Staphylococcus aureus* H 228 | 0.1 | 0.05 | 0.05 | 0.25 | 0.2 | 0.05 | 0.006 |
| *Staphylococcus aureus* UC-76 | 0.05 | 0.013 | 0.013 | 0.013 | 0.1 | 0.013 | 0.003 |
| *Streptococcus faecalis* MGH-2 | 0.8 | 0.1 | 0.2 | 0.05 | 0.2 | 0.1 | 0.013 |
| *Streptococcus pneumoniae* SV-1 | 0.05 | 0.025 | 0.013 | 0.013 | 0.1 | 0.05 | 0.003 |
| *Streptococcus pyogenes* C-203 | 0.1 | 0.05 | 0.025 | 0.025 | 0.4 | 0.05 | 0.003 |

The following nonlimiting examples illustrate the inventors' preferred methods for preparing the compounds of the invention.

PREPARATION OF STARTING MATERIALS

Example A 2-(2,3,4,5-Tetrafluoro-6-methylphenyl)-4,4-dimethyl-2-oxazoline

A solution of 21.2 g (80.0 mmol) of 2-(pentafluorophenyl)-4,4-dimethyl-2-oxazoline (Bull. Chem. Soc. Jpn., 57, 225 (1984)) in 300 mL of dry ether was cooled to −20° C. under argon and treated with 60 mL of 1.6M methyl lithium (96.0 mmol). The mixture was stirred at −20° C. for 2 hours, then stirred at room temperature overnight. The mixture was diluted with water, and the organic layer was dried over magnesium sulfate and concentrated to give 20.8 g of the title compound as an orange oil.

Example B 2,3,4,5-Tetrafluoro-6-methylbenzoic acid

A mixture of 20.5 g (73.4 mmol) of 2-(2,3,4,5-tetrafluoro-6-methylphenyl)-4,4-dimethyl-2-oxazoline in 200 mL of 6N hydrochloric acid was refluxed for 18 hours, then cooled to room temperature. The solution was extracted with ethyl acetate. The extract was washed with water, dried over magnesium sulfate, and concentrated. The residue was suspended in water which was made basic (pH 11) with 1M sodium hydroxide and was extracted with ether; the aqueous phase was acidified (pH 2) with 1N hydrochloric acid and extracted with ethyl acetate. The organic layer was dried over magnesium sulfate and concentrated to give 8.4 g of the title compound as a tan solid, mp 80°–82° C.

Example C 2,3,4,5-Tetrafluoro-6-methylbenzoyl chloride

A solution of 8.2 g (39.4 mmol) of 2,3,4,5-tetrafluoro-6-methylbenzoic acid, 6.0 g (47.2 mmol) of oxalyl chloride, and 100 mL of dichloromethane was treated with three drops of DMF. The solution was stirred for 3 hours, then concentrated to give 8.8 g of the title compound as a yellow liquid. The product was used as is in the next step.

Example D

Ethyl 3-(2,3,4,5-tetrafluoro-6-methylphenyl)-β-oxopropanoate

A solution of 10.1 g (76.5 mmol) of malonic acid monoethylester, bipyridyl (catalytic), and 200 mL of dry THF was cooled to −35° C. under argon, treated with 52 mL of 1.5M n-butyllithium (78 mmol), and warmed to −5° C. To this mixture was added 52 mL of 1.5M n-butyllithium (78 mmol) until a pale pink color persisted for 10 minutes. The suspension was cooled to −78° C. and was treated with a solution of 8.8 g (38.8 mmol) of 2,3,4,5-tetrafluoro-6-methylbenzoyl chloride in 100 mL of dry THF. The reaction mixture was stirred at −78° C. for 45 minutes, then warmed to −35° C. and poured into a mixture of ice and 1N hydrochloric acid (77 mL). The organic layer was washed with 5% sodium bicarbonate solution, 3M hydrochloric acid, and water and dried over magnesium sulfate. Concentration gave an orange oil which was chromatographed on silica gel (E. Merck 230–400 Mesh), eluting with 80:20 chloroform:ethyl acetate, to give 8.2 g of the title compound.

Example E

Ethyl 2-(2,3,4,5-Tetrafluoro-6-methyl-benzoyl)-3-ethoxyacrylate

A solution of 8.1 g (29.1 mmol) of ethyl 3-(2, 3,4,5-tetrafluoro-6-methylphenyl)-β-oxopropanoate, 7.2 g (43.3 mmol) of triethyl orthoformate, and 70 mL of acetic anhydride was refluxed for 3.5 hours. The solution was cooled to room temperature and concentrated under high vacuum to give 9.1 g of the title compound. The product was used as is in the next step.

Example F

Ethyl 2-(2,3,4,5-tetrafluoro-6-methylbenzoyl)-3-cyclo propylaminoacrylate

To a solution of 9.0 g (27.0 mmol) of ethyl 2- (2, 3, 4, 5-tetrafluoro-6-methylbenzoyl)-3-ethoxyacrylate in 30 mL of absolute ethanol at 5° C. was added 1.68 g (29.4 mmol) of cyclopropylamine. The mixture was stirred at 5° C. for 1.5 hours and at room temperature for 2.5 hours. The solution was concentrated to an oil which was triturated with hexane to give a tan solid. The crude product was recrystallized from hexane to give 9.07 g of the title compound, mp 72°–74° C.

Example G

Ethyl 1-cyclopropyl-6,7,8-trifluoro-1,4-dihydro-5-methyl-4-oxo-3-quinolinecarboxylate To a mixture of 9.05 g (26.3 mmol) of ethyl 2-(2,3,4,5-tetrafluoro-5-methylbenzoyl)-3-cyclopropylaminoacrylate in 100 mL of dry t-butanol was added a slurry of 3.25 g (29.0 mmol) of potassium t-butoxide in 20 mL of dry t-butanol, and the mixture was stirred at 60° C. for 4 hours. The suspension was cooled to room temperature and concentrated to a paste which was partitioned between dichloromethane and 1N hydrochloric acid. The organic layer was separated, dried over magnesium sulfate, and concentrated. Recrystallization from ethyl acetate:hexane gave 4.70 g of the title compound, mp 176°–177° C.

Example H

1-Cyclopropyl-6,7,8-trifluoro-1,4-dihydro-5-methyl-4-oxo-3-aminolinecarboxylic acid A mixture of 4.6 g (14.1 mmol) of ethyl 1-cyclopropyl-6,7,8-trifluoro-1,4-dihydro-5-methyl-4-oxo-3-quinolinecarboxylate in 100 mL of 6M hydrochloric acid was refluxed for 4 hours. The solution was cooled to room temperature and the solids were filtered, washed with water, and dried to give 3.9 g of the title compound, mp 234°–235° C.

In a similar manner, 1-cyclopropyl-5-ethyl-6,7,8-trifluoro-1,4-dihydro-4-oxo-3-quinolinecarboxylic acid and 1,5-dicyclopropyl-6,7,8-trifluoro-1,4-dihydro-4-oxo-3-quinolinecarboxylic acid were prepared.

Example I

N-(2-Hydroxy-1,1-dimethylethyl)-2,4,5-trifluorobenzamide

A solution of 19.4 g (110 mmol) of 2,4,5-trifluorobenzoic acid (JP 58,150,543 (Cl. C07C69) Sep. 7, 1983). 15.2 g (120 mmol) of oxalyl chloride and 250 mL of dichloromethane was treated with four drops of DMF, and the mixture was stirred at room temperature for 4 hours. The mixture was concentrated to a oil and was redissolved in 100 mL of dichloromethane. This solution was added dropwise to a solution of 19.6 g (240 mmol) of 3-amino-2-methyl-1-propanol in 200 mL of dichloromethane at 5° C., and the reaction mixture was stirred at room temperature overnight. The solids were filtered, and the filtrate was washed with 5% sodium bicarbonate, 1N hydrochloric acid, and water. The organic layer was dried over magnesium sulfate and concentrated to give 24.5 g of the title compound, mp 114°–116° C.

Example J 2-(2,4,5-Trifluorophenyl)-4,4-dimethyl-2-oxazoline

To a solution of 24.4 g (98.7 mmol) of N-(2-hydroxy-1,1-dimethylethyl)-2,4,5-trifluorocarboxamide in 200 mL of chloroform was added 25 mL (342 mmol) of thionyl chloride dropwise. The solution was stirred overnight at room temperature, then concentrated by half. The mixture was diluted with ether, and the solid was removed by filtration. This solid was dissolved in water, made basic (pH 8) with 10% sodium hydroxide, and extracted with ethyl acetate. The organic layer was dried over magnesium sulfate and concentrated to give 19.0 g of the title compound, mp 53°–54° C.

Example K 2-(2,4,5-Trifluoro-3-trimethylsilylphenyl)-4,4-dimethyl-2-oxazoline A solution of 8.7 mL (62.1 mmol) of diisopropylamine in 100 mL of dry THF under argon was cooled to −78° C. and treated with 28.3 mL (56.6 mmol) of 2.0M n-butyllithium. The LDA solution was stirred at −78° C. for 15 minutes. To this solution was added a solution of 11.8 g (51.5 mmol) of 2-(2,4,5-trifluorophenyl)-4,4-dimethyl-2-oxazoline in 50 mL of THF, and the reaction mixture was stirred for 1 hour at −78° C. To the reaction mixture was added 13 mL (102.5 mmol) of chlorotrimethylsilane, and the solution was warmed to room temperature. Water was added; the organic layer was dried over magnesium sulfate and concentrated. The crude product was chromatographed on silica gel (E. Merck 230–400 Mesh), eluting with 80:20 chloroform:ethyl acetate to give 12.9 g of the title compound, mp 71°–72° C.

Example L 2-(2,4,5,-Trifluoro-6-methyl-3-trimethylsilylphenyl)-4,4-dimethyl-2-oxazoline A solution of 0.64 mL (4.57 mmol) of diisopropylamine in 20 mL of dry THF under argon was cooled to −78° C. and treated with 2.1 mL (4.20 mmol) of 2.0N n-butyllithium. The LDA solution was stirred at −78° C. for 15 minutes, then warmed to 0° C. To this solution was added a solution of 1.05 g (3.5 mmol) of 2-(2,4,5- trifluoro-3-trimethylsilylphenyl)-4,4-dimethyl-2-oxazoline in 5 mL of THF; the reaction mixture was stirred at 0° C. for 45 minutes, then quenched with 1.50 g (10.6 mmol) of methyl iodide. The solution was stirred at room temperature for 3 hours and diluted with water. The organic layer was washed with water, dried over magnesium sulfate, and concentrated to give 1.00 g of the title compound as an oil.

In a similar manner, 1-cyclopropyl-5-ethyl-6,7-difluoro-1,4-dihydro-4-oxo-3-quinolinecarboxylic acid and 1-cyclopropyl-6,7-difluoro-1,4-dihydro-4-oxo-5-i-propyl-3-quinolinecarboxylic acid were prepared.

Alternatively, the trimethylsilyl group was displaced with chlorine (Chem. Abstr. 54, 20932 (1960)) or with bromine (J. Am. Chem. Soc. 70, 433 (1948)), and the oxazaline was hydrolyzed to give 3-chloro-2,4,5-trifluoro-6-methylbenzoic acid and 3-bromo-2,4,5-trifluoro-6-methylbenzoic acid, respectively. These intermediates were elaborated into 8-chloro-1-cyclopropyl-6,7-difluoro-1,4-dihydro-5-methyl-4-oxo-3-quinolinecarboxylic acid 8-bromo-1-cyclopropyl-6,7-difluoro-1,4-dihydro-5-methyl-4-oxo-3-quinolinecarboxylic acid.

In addition, the trimethylsilyl group was reacted with lead tetraacetate/trifluoroacetic acid to introduce a hydroxyl group (Tet. Lett. 10, 853 (1974)) and was also reacted with nitric acid to introduce a nitro group (J. Chem. Soc. 494 (1957)).

Following the usual procedures, the following compounds were prepared: 1-cyclopropyl-6, 7 -difluoro-1,4-dihydro-8-hydroxy-5-methyl-4-oxo-3-quinolinecarboxylic acid; 1-cyclopropyl-6,7-difluoro-1,4-dihydro-8-methoxy-5-methyl-4-oxo-3-quinolinecarboxylic acid; 1-cyclopropyl-6,7-difluoro-1,4-dihydro-5-methyl-8-nitro-4-oxo-3-quinolinecarboxylic acid, and 8-amino-1-cyclopropyl-6,7-difluoro-1,4-dihydro-5-methyl-4-oxo-3-quinolinecarboxylic acid.

Example M

7-Chloro-1-cyclopropyl-6-fluoro-1,4-dihydro-5-methyl-4-oxo-1,8-naphthyridine-3-carboxylic acid Ethyl 2,6-dichloro-5-fluoronicotinate (Chem. Pharm. Bull. 3.5.(6), 2280 (1987)) was treated with lithium diisopropylamide and quenched with methyl iodide to give, upon work-up, ethyl 2,6-dichloro-5-fluoro-4-methylnicotinate. This material was hydrolyzed to give the corresponding acid which was elaborated in the usual manner to give 7-chloro-1-cyclopropyl-6-fluoro-1,4-dihydro-5-methyl-4-oxo-1,8-naphthyridine-3-carboxylic acid. 7-chloro-1-cyclopropyl-5-ethyl-6-fluoro-1,4-dihydro-4-oxo-1,8-naphthyridine-3-carboxylic acid was synthesized in the same manner.

Example N 2,4,5-Trifluoro-3,6-dimethylbenzoic acid

The 2-(2,4,5-trifluorophenyl)-4, 4-dimethyl-2-oxazoline was also treated with lithium diisopropylamide followed by methyl iodide to give 2-(2,4,5-trifluoro-3-methylphenyl)-4, 4-dimethyl-2-oxazoline. This intermediate was, in turn, treated with lithium diisopropylamide, then with methyl iodide, to give 2-(2,4,5-trifluoro-3,6-dimethylphenyl)-4,4-dimethyl-2-oxazoline. Hydrolysis of the oxazoline gave 2,4,5-trifluoro-3,6-dimethylbenzoic acid, which was elaborated into 1-cyclopropyl-6,7-difluoro-1,4-dihydro-5,8-dimethyl-4-oxo-3-quinolinecarboxylic acid in the usual manner.

Example O 2-(2,4,5-Trifluoro-6-methylphenyl)-4,4-dimethyl-2-oxazoline

A solution of 12.0 g (38.0 mmol) of 2-[2,4,5-trifluoro-6-methyl-3-(trimethylsilyl)phenyl]-4,4-dimethyl-2-oxazoline, 5.85 g (38.5 mmol) of cesium fluoride, 110 mL of dimethylformamide, and 15 mL of water was stirred for 18 hours at room temperature. The reaction mixture was poured into water and extracted with ethyl acetate; the organic phase was washed with water, dried over magnesium sulfate, and concentrated to give 9.1 g of liquid.

Example P 2-(3-Chloro-2,4,5-trifluorophenyl)-4,4-dimethyl-2-oxazoline

A solution of 7.6 mL (54.2 mmol) of diisopropylamine in 100 mL of dry THF was cooled to −78° C. under argon, treated with 20.5 mL (47.2 mmol) of 2.3M n-butyllithium, and stirred for 15 minutes. To this solution was added a solution of 10.3 g (45.0 mmol) of 2-(2,4,5-trifluorophenyl)-4, 4-dimethyl-2-oxazoline in 100 mL of dry THF. The reaction mixture was stirred at −78° C. for 45 minutes. To this mixture was added 26.5 g (100 mmol) of hexachloroacetone, and the solution was warmed to room temperature. Water was added; the organic phase was washed with water, 1N hydrochloric acid, and 5% sodium bicarbonate, and was dried over magnesium sulfate. Concentration gave a dark oil which was chromatographed on silica gel to give 7.05 g of the title compound as a yellow oil.

Example Q 2-(3-Chloro-2,4,5-trifluoro-6-methyl-4,4-dimethyl-2-oxazoline

A solution of 5.5 mL (39.2 mmol) of diisopropylamine in 125 mL of dry THF was cooled to −78° C. under argon, treated with 13.8 mL (31.7 mmol) of 2.3M n-butyllithium, and stirred for 15 minutes. To this solution was added a solution of 7.00 g (26.5 mmol) of 2-(3-chloro-2, 4,5-trifluorophenyl)-4,4-dimethyl-2-oxazoline in 75 mL of dry THF. The mixture was stirred at −78° C. for 30 minutes and at 0° C. for 60 minutes. To this solution was added 11.3 g (79.6 mmol) of methyl iodide, and the mixture was stirred at room temperature overnight. Water was added; the organic phase was washed with 1N HCl, 5% sodium bicarbonate, and water. The solution was dried over magnesium sulfate and concentrated to an oil which was chromatographed on silica gel to give 6.3 g of clear orange oil.

Example R 2,4,5-Trifluoro-6-methylbenzoic acid

A mixture of 9.1 g (37.4 mmol) 2-(2,4,5-trifluoro-6-methylphenyl)-4,4-dimethyl-2-oxazoline in 200 mL of 6M hydrochloric acid was refluxed overnight, then cooled to room temperature. The solution was extracted with ethyl acetate, and the extract was washed with water, dried over magnesium sulfate, and concentrated. The residue was suspended in water which was made basic (pH 11) with 1N NaOH, washed with ether, and acidified (pH 2) with 1N HCl. The solution was extracted with ethyl acetate. The organic phase was washed with water, dried over magnesium sulfate, and concentrated to give 5.8 g of the title compound, mp 108°–110° C.

Example S

3-Chloro-2,4,5-trifluoro-6-methylbenzoic acid

As in Example D, the title compound was prepared from 2-(3-chloro-2,4,5-trifluoro-6-methylphenyl)-4,4-dimethyl-2-oxazoline and 6N hydrochloric acid. The desired acid was obtained as a tan solid, mp 104°–106° C.

Example T 2,4,5-Trifluoro-6-methylbenzoyl chloride

A solution of 5.8 g (30.5 mmol) of 2,4,5-trifluoro-6-methylbenzoic acid, 4.7 g (37.0 mmol) of oxalyl chloride, and 100 mL of dichloromethane was treated with three drops of DMF. The reaction mixture was stirred at room temperature for 2 hours, then concentrated to give 6.3 g of the title compound as an oily solid. The product was used "as is" in the next step.

Example U

3-Chloro-2,4,5-Trifluoro-6-methylbenzoyl chloride

The title compound was prepared from 3-chloro-2,4,5-trifluoro-6-methylbenzoic acid and oxalyl chloride following the same procedure used in Example F.

Example V

Ethyl 3-(2,4,5-trifluoro-6-methylbenzoyl)-β-oxopropanoate

A solution of 8.0 g (60.5 mmol) of malonic acid monoethylester, bipyridyl (catalytic) and 200 mL of dry THF was cooled to −35° C. under argon, treated with 32 mL of 1.9M n-butyllithium (60.8 mmol), and warmed to −5° C. To this suspension was added another 32 mL of 1.9M n-butyllithium until a pale pink color persisted for 10 minutes. The mixture was cooled to −78° C. To this mixture was added a solution of 6.3 g (30.2 mmol) of 2,4,5-trifluoro-6-methylbenzoyl chloride in 75 mL of dry THF, and the reaction mixture was stirred at −78° C. for 1 hour. The solution was then warmed to −35° C., poured onto a mixture of ice and 1N hydrochloric acid (70 mL), and extracted with ethyl acetate. The organic layer was washed with 5% sodium bicarbonate, 3M hydrochloric acid, and water, and was stirred over magnesium sulfate. Concentration gave an orange oil which was chromatographed on silica gel (E. Merck 230–400 Mesh), eluting with 80:20 chloroform:ethyl acetate, to give 7.2 g of the title compound.

Example W

Ethyl 3-(3-chloro-2,4,5-trifluoro-6-methylbenzoyl)-β-oxopropanoate

The procedure outlined for Example H was used to prepare the title compound from the dianion of malonic acid monoethyl ester and 3-chloro-2,4,5-trifluoro-6-methylbenzoyl chloride. The crude product was also chromatographed on silica gel to give the desired product as an orange oil.

Example X

Ethyl 2-(2,4,5-trifluoro-6-methylbenzoyl)-3-ethoxyacrylate

A solution of 7.1 g (27 mmol) of ethyl (3-2 (2,4,5-trifluoro-6-methylbenzoyl)-β-oxopropanoate, 6.8 g (41 mmol) of triethyl orthoformate and 60 mL of acetic anhydride was refluxed for 3 hours, cooled to room temperature, and concentrated to give 8.4 g of the title compound. The crude material was used as is in the next step.

Example Y

Ethyl 2-(3-chloro-2,4,5-trifluoro-6-methylbenzoyl)-3-ethoxy acrylate

The procedure outlined in Example J was followed to prepare the title compound from ethyl 3-(chloro-2,4,5-trifluoro-6-methylbenzoyl)-β-oxo-propanoate, triethyl orthoformate, and acetic anhydride.

Example Z

Ethyl 2-(2,4,5-trifluoro-6-methylbenzoyl)-3-cyclopropylaminoacrylate

To a solution of 8.3 g (26 mmol) of ethyl 2-(2,4,5-trifluoro-6-methylbenzoyl)-3-ethoxyacrylate in 30 mL of absolute ethanol at 5° C. was added 1.64 g (29 mmol) of cyclopropylamine. The reaction mixture was stirred at 5° C. for 90 minutes and at room temperature for 2 hours. The solution was concentrated to give a brown oil which was dissolved in hexane and reconcentrated to give a tan solid. Recrystallization from hexane gave 7.2 g of colorless crystals, mp 69°–72° C.

The following compounds were prepared in identical fashion from the appropriate ethoxyacrylate:
a) Ethyl 2-(3-chloro-2,4,5-trifluoro-6-methylbenzoyl)-3-cyclopropylaminoacrylate, mp 77°–80° C.;
b) Ethyl 2-(2,3,4,5-tetrafluoro-6-methylbenzoyl)-3-ethylaminoacrylate, hygroscopic solid;
c) Ethyl 3-(2,4-difluoroanilino)-2-(2,3,4,5-tetra-fluoro-6-methylbenzoyl)acrylate, viscous oil;
d) Ethyl 3-(2-bromoethylamino)-2-(2,3,4,5-tetrafluoro-6-methylbenzoyl)acrylate, mp 95°–100° C.;
e) Ethyl 3-(ethylamino)-2-(2,4,5-trifluoro-6-methylbenzoyl) acrylate, hygroscopic solid;
f) Ethyl 3-(2,4-difluoroanilino)-2-(2,4,5-trifluoro-6-methylbenzoyl)acrylate, mp 79°–83° C.; and
g) Ethyl 3-(2-bromoethylamino)-2-(2,4,5-trifluor-6-methylbenzoyl)acrylate.

Example AA

Ethyl 1-cyclopropyl-6,7-difluoro-1,4-dihydro-4-oxo-3-quinolinecarboxylate

A solution of 7.2 g (22 mmol) of ethyl 2-(2,4,5-trifluoro-5-methylbenzoyl)-3-cyclopropylaminoacrylate in 100 mL of dry t-butanol was treated portionwise with 2.8 g (25 mmol) of potassium t-butoxide, and the reaction mixture was stirred at 60° C. for 5 hours. The suspension was cooled to room temperature and concentrated. The residue was partitioned between dichloromethane and 1N hydrochloric acid; the organic phase was washed with water, dried over magnesium sulfate, and concentrated. The crude product was slurried in boiling ethanol, filtered, and air-dried to give 4.2 g of the title compound.

The following compounds were prepared in a similar fashion and purified as noted:
a) Ethyl 8-chloro-1-cyclopropyl-6,7-difluoro-1,4-difluoro-1,4-dihydro-5-methyl-4-oxo-3-quinolinecarboxylate, mp 151°–153° C. (chromatographed on silica gel);
b) Ethyl 1-ethyl-6,7,8-trifluoro-1,4-dihydro-5-methyl-4-oxo-3-quinolinecarboxylate, mp 185°–187° C. (recrystallized from ethyl acetate);
c) Ethyl 1-(2-bromoethyl)-6,7,8-trifluoro-1,4-dihydro-5-methyl-4-oxo-3-quinolinecarboxylate, mp 149°–150° c (recrystallized from ethyl acetate hexane).
d) Ethyl 1-ethyl-6,7-difluoro-1,4-dihydro-5-methyl-4-oxo-3-quinolinecarboxylate, mp 189°–191° C.

Example BB

Ethyl 6,7,8-trifluoro-1,4-dihydro-5-methyl-4-oxo-1-vinyl-3-quinolinecarboxylate

A rapidly stirred suspension of 1.98 g (5.08 mmol) of ethyl 1-(2-bromoethyl)-6,7,8-trifluoro-1,4-dihydro-5-methyl-4-oxo-3-quinolinecarboxylate, 3.50 g (25.3 mmol) of ground potassium carbonate, and 40 mL of DMF was heated at 80° C. under argon for 4 hours. The suspension was concentrated and the residue was partitioned between methylene chloride and water. The organic layer was dried over magnesium sulfate and concentrated to give 1.52 g of the title compound as a DMF complex, mp 150°–152° C.

Example CC

Ethyl 6,7,8-trifluoro-1-(2,4-difluorophenyl)-1,4-dihydro-5-methyl-4-oxo-3-quinolinecarboxylate To a cold (5° C.) solution of 2.77 g (6.64 mmol) of ethyl 3-(2,4-difluoroanilino)-2-(2, 3,4,5-tetrafluoro-6-methylbenzoyl)acrylate in 60 mL of dry THF was added 0.32 g of 60% sodium hydride. The solution was stirred overnight at room temperature, then concentrated to an orange foam. The residue was partitioned between methylene chloride and 1N HCl. The organic phase was washed with water, dried over magnesium sulfate, and concentrated to an orange solid which was recrystallized (ethyl acetate:hexane) to give 1.55 g of the title compound, mp 152°–154° C.

Example DD

Ethyl 6,7-difluoro-1-(2,4-difluorophenyl)-1,4-dihydro-5-methyl-4-oxo-3-quinolinecarboxylate The procedure outlined in Example AA was used to prepare the title compound from ethyl 3-(2,4-difluoroanilino)-2-(2,4,5-trifluoro-6-methylbenzoyl) acrylate, mp 161°–164° C.

Example EE

1-Cyclopropyl-6,7-difluoro-1,4-dihydro-4-oxo-3-quinolinecarboxylic acid

A suspension of 4.1 g (13.3 mmol) of ethyl 1-cyclopropyl-6,7-difluoro-1,4-dihydro-4-oxo-3-quinolinecarboxylate in 150 mL of 6N hydrochloric acid was refluxed for 6 hours, then cooled to room temperature. The solids were filtered, washed with water and ether, and dried to give 3.2 g of the title compound, mp>300° C.

The following compounds were prepared in a similar fashion:
a) 1-Ethyl-6,7,8-trifluoro-1,4-dihydro-5-methyl-4-oxo-3-quinolinecarboxylic acid, mp 199°–201° C.;
b) 1-Ethyl-6,7-difluoro-1,4-dihydro-5-methyl-4-oxo-3-quinolinecarboxylic acid., mp>300° C.;
c) 8-Chloro-1-cyclopropyl-6,7-difluoro-1,4-dihydro-5-methyl-4-oxo-3-quinolinecarboxylic acid, mp 212°–214 ° C.

Example FF

7-Chloro-1-cyclopropyl-6-fluoro-1,4-dihydro-4-oxo-1,8-naphthyridine-3-carboxylic acid ethyl ester 7-Chloro-1-cyclopropyl-6-fluoro-1,4-dihydro-4-oxo-1,8-naphthyridine-3-carboxylic acid, (U.S. Pat. No. 4,663,457) (20.0 g, 71 mmol) and dimethylformamide (0.5 mL) were added to dichloromethane (750 mL) to give a tan slurry. Oxalyl chloride (7.4 mL, 85 mmol) was added to this slurry over one minute and the reaction mixture stirred for 90 minutes, then an additional 2.0 mL of oxalyl chloride was added and stirring continued for 60 minutes. To the resulting brown solution was added absolute ethanol (4.3 mL, 78 mmol) and the mixture stirred for 4 hours and then cooled to 0° C. and stored overnight. The reaction was warmed to room temperature and an additional 2 mL of absolute ethanol was added and the stirring continued for 3 hours. The reaction was evaporated to a brown solid. The solid was heated in THF, filtered, and cooled to 0° C. The crystals formed were collected and dried to give the title compound (11.1 g, 50%).

Example GG

7-Chloro-1-cyclopropyl-6-fluoro-1,2,3,4-tetrahydro-4-oxo-1,8-naphthyridine-3-carboxylic acid ethyl ester, 3

In absolute ethanol (200 mL) was suspended the compound prepared in Example FF (3.0 g, 9.6 mmol) and sodium cyanoborohydride (0.7 g, 10 mmol) and three drops of concentrated HCl was added, giving a bright yellow solution. As the reaction progressed and was monitored by TLC (silica gel, $CH_2Cl_2/CH_3OH$ 9:1 v/v) additional aliquots of concentrated HCl were added as needed to maintain the progress of the reaction. After 6 hours the reaction was quenched by adding it to 300 mL of water. The mixture was extracted several times with $CH_2Cl_2$ and the combined organic layers dried, filtered, and evaporated to a yellow solid. This solid was filtered through silica gel with $CH_2Cl_2$ and after evaporation the solid was crystallized from isopropyl ether. The collected crystals were further purified by column chromatography on silica gel with $CH_2Cl_2$ to give the title compound (2.2 g, 73%).

The following compound was prepared in the same manner:
a) 7-chloro-6-fluoro-1-(2,4-difluorophenyl)-1,2,3,4-tetrahydro-4-oxo-1,8-naphthyridine-3-carboxylic acid ethyl ester

Example HH

7-Chloro-6-cyclopropyl-6-fluoro-2,3,4-tetrahydro-5-methyl-4-oxo-1,8-naphthyridine-3-carboxylic acid ethyl ester Compound GG (4.5 g, 14 mmol) was dissolved in THF (170 mL) and cooled to <−70° C. Then sec-butyl lithium (22.2 mL, 28 mmol, 1.3M) was added dropwise over 30 minutes, always keeping the internal temperature <−70° C. After stirring at −70° C. for 1 hour, methyl iodide (0.9 mL, 14 mmol) was added and the reaction stirred at −70° C. for 7 hours. The reaction flask was transferred to a Dewar containing dry ice/isopropanol and allowed to stand for 17 hours. At the end of this time period the reaction temperature had warmed to −25° C. The reaction was quenched by the addition of saturated NH$_4$Cl solution (50 mL) and diluted with an equal volume of CH$_2$Cl$_2$. The organic layer was separated and washed with saturated NaCl solution, dried, filtered, and evaporated to an oil. This oil was purified by column chromatography on silica gel with CH$_2$Cl$_2$ to give, after combining and evaporating the appropriate fraction, the title compound (3.91 g, 85%).

Example II

7-Chloro-1-cyclopropyl-6-fluoro-1,4-dihydro-5-methyl-4-oxo-1,8-naphthyridine-3-carboxylic acid ethyl ester Using the procedure of Reich, et al, J. Amer. Chem. Soc., (1975) 97, 5434, the compound prepared in Example HH (0.68 g, 2.1 mmol) was converted into the title compound (0.44 g, 64%). Purification was achieved by crystallization from isopropyl ether.

Example JJ

3-Bromo-2,5,6-trifluorobenzoic acid n-Butyl lithium (2.6M in hexanes, 32 mL, 84 mmol) was added over 10 minutes to a solution of diisopropylamine (8.89 g, 88 mmol) in THF (80 mL) stirred under N$_2$ at 0° C. After a further 10 minutes at 0°, the solution was transferred by catheter over 40 minutes to a solution of 2,4,5-trifluoro-bromobenzene (16.88 g, 80 mmol) in THF (200 mL) stirred under N$_2$ at −78° C. After a further 15 minutes the solution was blown through a catheter over ~2 minutes onto a slurry of CO$_2$ (~200 mL) in ether (400 mL) with vigorous stirring. When the CO$_2$ evaporated the slurry was washed with dilute HCl (1M, 200 mL) and water (100 mL). The organic phase was extracted with dilute NaOH (0.5M, 2×100 mL). The aqueous phase was extracted with ether (2×100 mL), and the combined organic phases were washed with water (100 mL), saturated brine (100 mL), and dried (MgSO$_4$). The solvent was removed under reduced pressure to give 3-bromo-2,5,6-trifluorobenzoic acid (17.25 g, 84.5%) as white microcrystalline needles; mp 114°–6° C. (sublimation).

Example KK

1-Bromo-2,4,5-trifluoro-3-(trifluormethyl)benzene

3-Bromo-2,5,6-trifluorobenzoic acid (16.92 g, 66 mmol) was heated with SF$_4$ (60 g) and HF (30 g) in a stainless steel bomb at 120° C. for 8 hours. When the reaction cooled to 25° C., the volatiles were vented through KOH traps, and when gas evolution ceased the vessel was extracted with CH$_2$Cl$_2$ (150 mL). This solution was washed with diluted NaHCO$_3$ solution (saturated/2, 50 mL), saturated brine (50 mL), and dried (MgSO$_4$). The solvent was removed by distillation through a 15-cm Vigreux column, and the residue was distilled under N$_2$ through a shortpath stillhead at 147°–150° C. to give 1-bromo-2,4,5-trifluoro-3-(trifluoromethyl)benzene (15.79 g, 83%) as a pale yellow oil. NMR (CDCl$_3$) δ 7.67 (1H, d of t, J$_d$=6 Hz, J$_t$=8.1 Hz, aromatic).

Example LL 2,4,5-Trifluoro-3-(trifluoromethyl)benzoic acid

A solution of n-butyl lithium (2.6M in hexanes, 9.6 mL, 25 mmol) was added dropwise through an addition funnel over 15 minutes to a solution of 1-bromo-2,4-5-trifluoro-3-(trifluoromethyl) benzene (7.00 g, 25 mmol) in ether (100 mL) stirred under N$_2$ at −78° C. After 5 minutes the mixture was rapidly blown by catheter onto a suspension of dry ice (100 g) in ether (100 mL). After 5 minutes TFA (2 mL) was added to this. When the solution had warmed up to 20° C., it was washed with diluted HCl (0.5M, 20 mL), and extracted with dilute base (0.5N, 2×50 mL). The combined basic extracts were washed with ether (25 mL), made acidic with concentrated HCl (~4 mL), and extracted with ether (3×50 mL). The combined ethereal extracts were washed with water (50 mL), saturated brine (50 mL), and dried (MgSO$_4$). The solvent was removed under reduced pressure to give 2,4,5-trifluoro-3-(trifluoromethyl)benzoic acid (4.21 g, 69%) as white microscopic needles; mp 87°–90° C. NMR (CDCl$_3$) δ 11.80 (1H, br s, OH), 8.05 (1H, d of t, J$_d$=6 Hz, J$_t$=9 Hz, aromatic).

Example MM

N-(2-Hydroxy-1,1-dimethylethyl)-2,4,5-trifluoro-3-trifluoromethyl)benzamide

A solution of 4.88 g (20.0 mmol) of 2,4,5-trifluoro-3-(trifluoromethyl) benzoic acid, 2.80 g (22.0 mmol) of oxalyl chloride, and 50 mL of methylene chloride was treated with 1 drop of DMF and stirred at room temperature for 4 hours. The solution was concentrated to a yellow oil which was dissolved in methylene chloride (20 mL) and added to a cold (ice bath) solution of 2.53 g (25 mmol) of triethylamine, 1.96 g (22 mmol) of 2-amino-2-methyl-1-propanol, and 40 mL of methylene chloride. The mixture was allowed to warm slowly to room temperature overnight. The solution was poured into 50 mL of 1N HCl, and the organic layer was separated and washed with water. The solution was dried over magnesium sulfate and concentrated to give 5.81 g of the title compound as a yellow oil.

Example NN

2-[2,4,5-Trifluoro-3-(trifluoromethyl)phenyl]-4,4-dimethyl-2-oxazoline

A solution of 5.81 g (18.4 mmol) of N-(2-hydroxy-1,1-dimethylethyl)-2, 4,5-trifluoro-3-(trifluoromethyl)benzamide in 100 mL of chloroform at 0° C. was treated dropwise with 5 mL of thionyl chloride. The mixture was allowed to warm to room temperature overnight. The solution was concentrated to a yellow oil which was dissolved in 20 mL of DMF and treated with 0.8 g (21.6 mmol) of 60% sodium hydride. This reaction mixture was stirred at room temperature for 18 hours, then poured into 50 mL of dilute NaHCO$_3$. The solution was extracted with ethyl acetate; the organic phase was washed with water and dried over magnesium sulfate. Concentration in vacuo gave an orange oil which was chromatographed on silica, eluting with 2% methanol in chloroform, to give 2.62 g of a yellow oil.

Example OO 2-2,4,5-Trifluoro-3-(trifluoromethyl)-6-methylphenyl]-4,4-dimethyl-2-oxazoline A solution of 1.12 g (11.0 mmol) of diisopropylamine in 5 mL of THF was cooled to 0° C. under nitrogen, treated with 4.0 mL of 2.5M n-butyllithium, and stirred for 10 minutes. This lithium diisopropylamide solution was added dropwise to a solution of 2.36 g (5 mmol) of 2-[2,4,5-trifluoro-3-(trifluoromethyl)phenyl]-4,4-dimethyl-2-oxazoline in 5 mL of THF at −78° C. The solution was stirred at −78° C. for 1 hour, then quenched with 2.24 g (16 mmol) of methyl iodide. The mixture was allowed to warm slowly to room temperature, stirred for 1 hour, and poured into 10 mL of 1N HCl. This solution was extracted with ether, and the extract was washed with water, dried over magnesium sulfate, and concentrated to give 2.28 g of the title compound.

Example PP 3-(Exo-amino)-8-azabicyclo[3.2.1]octane, dihydrochloride

A mixture of 4.6 g (20 mmole) of 8-(phenylmethyl)-8-azabicyclo[3.2.1]octan-3-one, oxime [J. R. Bagley and T. N. Piley, J. Heterocyclic Chem., 19, 485 (1982)], 0.5 g of 10% rhodium on carbon, and 100 mL of acetic acid was hydrogenated until the requisite amount of hydrogen was taken up. The reaction mixture was filtered and two equivalents of HCl was added. The solid was filtered to yield 2.80 g of the title compound, mp >300° C.

Example QQ 3-(Endo-amino)-8-azabicyclo[3.2.1]octane, dihydrochloride

A solution of 7.33 g (25 mmol) of 3-(endoamino)-8-(phenylmethyl)-8-azabicyclo[3.2.1]octane dihydrochloride [P. Dosteft et al, Eur. J. Med. Chem.-Chim. Ther., 19, 105 (1984)], 1.0 g of 20% palladium on carbon and 100 mL of methanol was hydrogenated until the required amount of hydrogen was taken up. The reaction mixture was filtered and the filtrate was evaporated to 4.5 g of the title compound which was used without purification.

Example RR 2,6-Dichloro-4-methyl-5-fluoronicotinic acid

To a solution of 0.516 moles of lithiodiisopropyl amine in 390 mL hexane and 200 mL tetrahydrofuran, cooled to −70° C., was added dropwise a solution of 40 g (0.229 moles) 2,6-dichloro-5-fluoronicotinic acid in 600 mL tetrahydrofuran, over a 1-hour period. The reaction mixture was stirred at −70° C. for 1 hour, then warmed to −60° C. for 1.5 hours at which time a light colored precipitate formed. The slurry was briefly warmed to −50° C., then recooled to −70° C., at which point a solution of 84 mL (1.34 moles) methyl iodide in 90 mL tetrahydrofuran was added dropwise. After the addition was complete, the reaction mixture was allowed to slowly warm to −20° C. over approximately 1 hour. The solution was acidified with dilute HCl pH 1–2 diluted with diethyl ether and allowed to warm to room temperature. The aqueous layer was extracted twice with ether. The combined ether washes were washed with $H_2O$, dried with $MgSO_4$, and evaporated in vacuo to yield a crude solid. The crude material was recrystallized from toluene to yield 31.7 g of the title compound.

Example SS 2,6-Dichloro-4-methyl-5-fluoronicotinic acid chloride

A slurry of 30.8 g (0.147 moles) of 2,6-dichloro-4-methyl-5-fluoronicotinic acid in 200 mL of dichloromethane, containing a catalytic amount of dimethyl formamide, was treated dropwise over a 1-hour period with 19.2 mL (0.22 moles) oxalyl chloride. After 1 hour, the homogenous solution was evaporated in vacuo, diluted with an equal volume of dichloromethane, and evaporated in vacuo to yield 31.6 g of the title compound as an oil.

Example TT

Ethyl 3-(2,6-dichloro-4-methyl-5-fluoropyridinyl)-3-oxo-2-carboxyethylpropanoate A suspension of 4.5 g of magnesium turning (0.188 moles) in 5 mL of carbon tetrachloride and 11 mL of ethanol was treated dropwise with 30.1 g (0.188 moles) of diethyl malonate in 20 mL of ethanol at such a rate to maintain a gentle reflux. The mixture was heated at reflux for an additional 1.5 hours. The slurry was cooled to room temperature and diluted with 150 mL of d/ethyl ether. The resulting solution was cooled to 0° C. and treated dropwise with 31.6 g of the product from Example SS in 60 mL of ether. Mixing continued for 15 minutes after the completion of the addition and the mixture was stirred at room temperature for an additional hour. The mixture was poured into 250 mL of $H_2O$/10 mL of concentrated $H_2SO_4$. The mixture was extracted twice with ether. The combined ether extracts were washed with $H_2O$, dried over $MgSO_4$, and evaporated in vacuo to yield 56.4 g of the title compound.

Example UU

Ethyl 3-(2,6-dichloro-4-methyl-5-fluoropyridinyl)-3-oxopropanoate

A suspension of 50.6 g (0.147 moles) of the product from Example TT in 350 mL of $H_2O$ containing 11.0 g p-toluenesulfonic acid hydrate was heated to reflux for a total of 3 hours. The suspension was cooled and diluted with diethyl ether. The ethereal layer was extracted with saturated $NaHCO_3$, water, and then dried with $MgSO_4$. After evaporation of the ether, 33.6 g (78%) of the title compound was obtained as an oil.

Example VV

Ethyl 3-(2,6-dichloro-4-methyl-3-fluoro-5-pyridinyl)-3-oxo-2-ethoxymethylenepropanoate A mixture of 33.6 g (0.114 moles) of the keto ester from Example UU, 200 mL of acetic anhydride, and 30 mL (0.171 mole) of triethyl orthoformate was refluxed with external heat for a total of 4 hours. The mixture was concentrated in vacuo, redissolved in an equal volume of ethanol, and again concentrated in vacuo to yield 38.5 g of the title compound as an oil.

Example WW

Ethyl 2-(2,4-difluorophenylaminomethylene)-3-(2,6-dichloro-3-fluoro-4-methyl-5-pyridyl)-3-oxopropanoate A solution of 12.0 g (34 moles) of the product from Example VV, 30 mL of ethanol, and 10 mL of hexane was cooled to 0° C. and treated dropwise with 3.5 mL of 2,4-difluoroaniline dissolved in 5 mL of ethanol and 5 mL of hexane. After mixing for 1 hour at 0° C., a precipitate began to form. The suspension was allowed to mix at room temperature for 2 hours, during which time 10 mL of hexane was added to facilitate mixing. Filtration of the resulting solid afforded 3.6 g of the title compound. The mother liquors were purified on a silica gel column (hexane/ethyl acetate 80/20) to yield an additional 4.5 g of the title compound.

Example XX

Ethyl 7-chloro-1-(2,4-difluorophenyl)-1,4-dihydro-5-methyl-1,8-naphthyridine-3-carboxylate A solution of 8.0 g (18.8 mmol) of the product from Example WW in 100 mL of 1,4-dioxane was treated portionwise with 0.8 g (20.7 mmol) of 60% NaH (oil suspension). The mixture was stirred at room temperature for 1.5 hours, then warmed to 50° C. for 0.5 hours. The mixture was cooled and quenched with dilute hydrochloric acid. After evaporation, the residue was dissolved in ethyl acetate and washed with $H_2O$, dried with $MgSO_4$ and concentrated in vacuo. The residue was purified by column chromatography (silicon gel dichloromethane/ethanol 95:5) to yield 2.94 g of the title compound.

Example YY

Ethyl 2-((Cyclopropyl)aminomethylene)-3-(2,6-dichloro-3-fluoro-4-methyl-5-pyridyl)-3-oxopropanoate A solution of 26.4 g (75 mmol) of the product in Example VV in 65 mL of ethanol and 15 mL of hexane, cooled to 0° C., was treated dropwise with a solution of 4.7 g (83 mole) of cyclopropyl amine in 10 mL of ethanol and 5 mL of hexane. The solution was stirred at 0° C. for 1 hour and stirred for 2 hours at room temperature. After evaporation of the solvents in vacuo, the residue was purified by column chromatography (silica gel hexane-ethyl acetate 8:2) to afford 13.3 g of the title compound.

Example ZZ

Ethyl 7-chloro-1-cyclopropyl-1,4-dihydro-6-fluoro-5-methyl-4-oxo-1,8-naphthyridine-3-carboxylate A solution of 13.1 g (36.3 mmole) of the product from Example YY is 300 mL of 1,4-dioxane is treated portionwise with 1.5 g (38.1 mmole) 60% NaH (oil suspension) at room temperature. The mixture was stirred for 1 hour at room temperature, then heated to 50° C. for 0.5 hours. The cooled solution was quenched with dilute hydrochloric acid and the solvent evaporated in vacuo. The residue was dissolved in ethyl acetate, washed with $H_2O$, dried with $MgSO_4$, and concentrated in vacuo. The crude residue was purified by column chromatography (silica gel methylene chloride/ethanol 95:5) to afford 10.8 g of the title compound, mp 170°–171° C. The product is identical to the material prepared in Example II.

Example 1

1-Cyclopropyl-6,8-difluoro-1,4-dihydro-5-methyl-4-oxo-7-(1-piperazinyl)-3-quinolinecarboxylic acid A suspension of 0.85 g (2.85 mmol) of 1-cyclopropyl-6,7,8-trifluoro-1,4-dihydro-5-methyl-4-oxo-3-quinolinecarboxylic acid, 1.00 g (11.6 mmol) of anhydrous piperazine, and 20 mL of acetonitrile was refluxed for 5 hours, then stirred at room temperature overnight. The precipitate was removed by filtration, washed with water and acetonitrile, and dried in vacuo to give 0.91 g of the title compound, mp 205°–206° C.

Example 2

7-(3-Amino-1-pyrrolidinyl)-1-cyclopropyl-6,8-difluoro-1,4-dihydro-5-methyl-4-oxo-3-quinolinecarboxylic acid A mixture of 1.00 g (3.36 mmol) of 1-cyclopropyl-6,7,8-trifluoro-1,4-dihydro-5-methyl-4-oxo-3-quinolinecarboxylic acid, 0.63 g (3.38 mmol) of 3-(t-butoxycarbonyl)aminopyrrolidine, 1.00 g (9.91 mmol) of triethylamine, and 35 mL of acetonitrile was refluxed for 5 hours, then stirred at room temperature overnight. The precipitate was removed by filtration and washed with acetonitrile and ether. The crude product was suspended in 20 mL of 6M hydrochloric acid and 20 mL of glacial acetic acid and was heated at 60° C. for 2 hours. The solution was concentrated to an oil which was triturated with isopropanol. The solid was collected by filtration and washed with ether to give 1.04 g of the title compound as the hydrochloride salt, mp>300° C.

Example 3

1-Cyclopropyl-7-[3-[(ethylamino)methyl]-1-pyrrolidinyl]-6,8-difluoro-1,4-dihydro-5-methyl-4-oxo-3-quinolinecarboxylic acid A mixture of 0.80 g (2.70 mmol) of 1-cyclopropyl-6,7,8-trifluoro-1,4-dihydro-5-methyl-4-oxo-3-quinolinecarboxylic acid, 0.41 g (3.20 mmol) of N-ethyl-3-pyrrolidinemethanamine, 0.82 g (8.10 mmol) of triethylamine, and 25 mL of acetonitrile was refluxed for 4 hours, then stirred at room temperature overnight. The precipitate was collected by filtration, washed with acetonitrile and ether, and dried to give 0.90 g of the title compound, mp 198°–199° C.

Example 4

7-[3-(Aminomethyl)-3-methyl-1-pyrrolidinyl]-1-cyclopropyl-6,8-difluoro-1,4-dihydro-5-methyl-4-oxo-3-quinolinecarboxylic acid A mixture of 0.60 g (2.02 mmol) of 1-cyclopropyl-6,7,8-trifluoro-1,4-dihydro-5-methyl-4-oxo-3-quinolinecarboxylic acid, 0.28 g (2.45 mmol) of 3-methyl-3-pyrrolidinemethanamine, 0.61 g (6.06 mmol) of triethylamine, and 20 mL of acetonitrile was refluxed for 4 hours, then stirred at room temperature overnight. The precipitate was removed by filtration, washed with ether, and dried in vacuo to give 0.61 g of the title compound, mp 182°–184° C.

Example 5

1-Cyclopropyl-6,8-difluoro-1,4-dihydro-5-methyl-7-[3-methyl-1-piperazinyl]-4-oxo-3-quinolinecarboxylic acid A suspension of 0.80 g (2.69 mmol) of 1-cyclopropyl-6,7,8-trifluoro-1,4-dihydro-5-methyl-4-oxo-3-quinolinecarboxylic acid, 1.08 g (10.8 mmol) of 2-methylpiperazine, and 20 mL of acetonitrile was refluxed for 3 hours, then cooled in an ice bath. The precipitate was collected, washed with water and acetonitrile, and dried in vacuo to give 0.76 g of the title compound, mp 187°–188° C.

Example 6

1-Cyclopropyl-6-fluoro-1,4-dihydro-5-methyl-4-oxo-7-(1-piperazinyl)-3-quinolinecarboxylic acid A suspension of 0.70 g (2.50 mmol) of 1-cyclopropyl-6,7-difluoro-1,4-dihydro-5-methyl-4-oxo-3-quinolinecarboxylic acid, 0.86 g (10.0 mmol) of anhydrous piperazine and 20 mL of acetonitrile was refluxed for 5 hours, then stirred at room temperature overnight. The precipitate was collected by filtration, washed with water and acetonitrile, and dried in vacuo to give 0.85 g of the title compound, mp 226°–228° C.

Example 7

1-Cyclopropyl-6-fluoro-1,4-dihydro-5-methyl-7-(3-methyl-1-piperazinyl)-4-oxo-3-quinolinecarboxylic acid A mixture of 0.75 g (2.68 mmol) of 1-cyclopropyl-6,7-difluoro-1,4-dihydro-5-methyl-4-oxo-3-quinolinecarboxylic acid, 1.07 g (10.4 mmol) of 2-methylpiperazine and 30 mL of acetonitrile was refluxed for 5 hours, then stirred at room temperature overnight. The precipitate was collected by filtration, washed with water/ethanol and acetonitrile, and dried in vacuo to give 0.42 g of the title compound, mp 189°–192° C.

Example 8

7-(3-Amino-1-pyrrolidinyl)-1-cyclopropyl-6-fluoro-1,4-dihydro-5-methyl-4-oxo-3-quinolinecarboxylic acid A mixture of 0.70 g (2.50 mmol) of 1-cyclopropyl-6,7-difluoro-1,4-dihydro-5-methyl-4-oxo-3-quinolinecarboxylic acid, 0.56 g (3.00 mmol) of 3-(t-butoxycarbonyl) aminopyrrolidine, 0.76 g (7.52 mmol) of triethylamine, and 25 mL of acetonitrile was refluxed for 4.5 hours, then stirred at room temperature overnight. The solids were collected by filtration and washed with acetonitrile and ether. The crude product was dissolved in 20 mL of 6N hydrochloric acid and 20 mL of acetic acid and was stirred at room temperature for 3 hours. The solution was concentrated to an oil which was triturated with 2:1 ether:isopropanol. The solids were removed by filtration, washed with ether, and dried to give 0.95 g of the title compound as the hydrochloride salt, mp>300° C.

Example 9

7-[3-(Aminomethyl)-3-methyl-1-pyrrolidinyl]-1-cyclopropyl-6-fluoro-1,4-dihydro-5-methyl-4-oxo-3-quinolinecarboxylic acid A mixture of 0.61 g (2.18 mmol) of 1-cyclopropyl-6,7-difluoro-1,4-dihydro-5-methyl-4-oxo-3-quinolinecarboxylic acid, 0.56 g (2.61 mmol) of 3-[(t-butoxycarbonyl)aminomethyl]-3-methylpyrrolidine, 0.66 g (6.54 mmol) of triethylamine, and 25 mL of acetonitrile was refluxed for 6 hours, then stirred overnight at room temperature. The precipitate was collected by filtration and washed with acetonitrile and ether. The crude product was suspended in 20 mL of 6N hydrochloric acid and 20 mL of glacial acetic acid and was stirred at room temperature for 3 hours. The solution was concentrated and the residue was triturated with ether. The solid was removed by filtration, washed with ether, and dried to give 0.61 g of the title compound as the hydrochloride, mp 250°–252° C.

Example 10

8-Chloro-1-cyclopropyl-6-fluoro-1,4-dihydro-5-methyl-4-oxo-7-(1-piperazinyl)-3-quinolinecarboxylic acid A suspension of 0.38 g (1.21 mmol) of 8-chloro-1-cyclopropyl-6,7-difluoro-1,4-dihydro-5-methyl-4-oxo-3-quinolinecarboxylic acid, 0.42 g (4.88 mmol) of piperazine and 20 mL of acetonitrile was refluxed for 4 hours, and then stirred at room temperature overnight. The precipitate was collected by filtration, washed with water and acetonitrile, and dried in vacuo to give 0.32 g of the title compound, mp 234°–235° C.

Example 11

7-(3-Amino-1-pyrrolidinyl)-8-chloro-1-cyclopropyl-6-fluoro-1,4-dihydro-5-methyl-4-oxo-3-quinolinecarboxylic acid A mixture of 0.50 g (1.60 mmol) of 8-chloro-1-cyclopropyl-6,7-difluoro-1,4-dihydro-5-methyl-4-oxo-3-quinolinecarboxylic acid, 0.36 g (1.93 mmol) of 3-(t-butoxycarbonyl) aminopyrrolidine, 0.48 g (4.75 mmol) of triethylamine, and 20 mL of acetonitrile was refluxed for 4 hours, then stirred at room temperature overnight. The solution was concentrated and the residue was triturated with ether:hexane (1:1) and filtered. The solid was washed with water and hexane. The crude product was suspended in 15 mL of dichloromethane and 1.5 mL of trifluoroacetic acid and was stirred at room temperature for 4 hours. The solution was concentrated to a gold solid which was suspended in water, made basic (pH 11) with 10% sodium hydroxide, and filtered. The solution was then neutralized (pH 7.1), and the precipitate was collected by filtration, washed with water, and dried in vacuo to give 0.29 g of the title compound, mp 124°–126° C.

Example 12

1-Ethyl-6,8-difluoro-1,4-dihydro-5-methyl-4-oxo-7-(1-piperazinyl)-3-quinolinecarboxylic acid A mixture of 0.45 g (1.58 mmol) of 1-ethyl-6,7,8-trifluoro-4-dihydro-5-methyl-4-oxo-3-quinolinecarboxylic acid, 0.54 g (6.27 mmol) of anhydrous piperazine, and 20 mL of acetonitrile was refluxed for 3 hours, then cooled to room temperature. The solids were collected by filtration, washed with water, acetonitrile, and ether to give 0.48 g of the title compound, mp 223°–225° C.

Example 13

7-(3-Amino-1-pyrrolidinyl)-1-ethyl-6,8-difluoro-1,4-dihydro-5-methyl-4-oxo-3-quinolinecarboxylic acid A mixture of 0.36 g (1.25 mmol) of 1-ethyl-6,7,8-trifluoro-1,4-dihydro-5-methyl-4-oxo-3-quinolinecarboxylic acid, 0.26 g (1.39 mmol) of 3-(t-butoxycarbonyl) aminopyrrolidine, 0.38 g (3.76 mmol) of triethylamine, and 20 mL of acetonitrile was refluxed for 5 hours, then stirred at room temperature overnight. The solids were collected by filtration and washed with acetonitrile and ether. The crude product was dissolved in 5 mL of 6N hydrochloric acid and 5 mL of glacial acetic acid and stirred for 5 hours at room temperature. The solution was concentrated to a solid which was suspended in water, made basic (pH 12), filtered through a fiberglass pad, and neutralized (pH 6.8). The solids were collected by filtration, washed with water, and dried in vacuo to give 0.32 g of white solid, mp 218°–220° C.

Example 14

6,8-Difluoro-1-(2,4-difluorophenyl)-1,4-dihydro-5-methyl-4-oxo-7-(1-piperazinyl)-3-quinolinecarboxylic acid A solution of 0.43 g (1.08 mmol) of ethyl 6,7,8-trifluoro-1-(2,4-difluorophenyl)-1,4-dihydro-5-methyl-4-oxo-3-quinolinecarboxylic acid, 0.37 g (4.30 mmol) of anhydrous piperazine, and 20 mL of acetonitrile was refluxed overnight, cooled to room temperature, and concentrated in vacuo. The residue was taken up in 10 mL of 6N hydrochloric acid and refluxed for 2 hours. The mixture was cooled and the solids were collected by filtration. The crude product was suspended in water which was made basic (pH 12), and the resulting solution was filtered through a fiberglass pad, and neutralized (pH 6.5). The solids were collected by filtration, washed with water, ether, and dried to give 0.37 g of the title compound, mp 283°–284° C.

The following compound was prepared following the same procedure:

a) 6,8-Difluoro-1-(2,4-difluorophenyl)-1,4-dihydro-5-methyl-7-(3,5-dimethyl-1-piperazinyl)-4-oxo-3-quinolinecarboxylic acid, mp 240°–242° C.

Example 15

7(3-Amino-1-pyrrolidinyl)-6,8-difluoro-1-(2,4-difluorophenyl)-1,4-dihydro-5-methyl-4-oxo-3-quinolinecarboxylic acid A solution of 0.40 g (1.00 mmol) of ethyl 6,7,8-trifluoro-1-(2,4-difluorophenyl)-1,4-dihydro-5-methyl-4-oxo-3-quinolinecarboxylic acid, 0.22 g (1.18 mmol) of 3-t-butoxycarbonylaminopyrrolidine, 0.30 g (3.00 mmol) of triethylamine, and 15 mL of acetonitrile was refluxed for 18 hours. The mixture was cooled and concentrated. The residue was dissolved in 10 mL of 6N hydrochloric acid; refluxed for 3 hours, and cooled to room temperature. The solids were filtered, washed with water and ether, and suspended in water. The suspension was made basic (pH 12) and the resulting solution was filtered through a fiberglass pad, and the filtrate was neutralized to pH 6.7. The solids were filtered and washed with water and ether to give 0.38 g of the title compound, mp 230°–232° C.

Example 16

6,8-Difluoro-1,4-dihydro-5-methyl-4-oxo-7-(1-piperazinyl)-1-vinyl-3-quinolinecarboxylic acid A solution of 0.69 g (1.80 mmol) of ethyl 6,7,8-trifluoro-1,4-dihydro-5-methyl-4-oxo-1-vinyl-3-quinolinecarboxylate, 0.62 g (7.2 mmol) of anhydrous piperazine, and 20 mmol of acetonitrile was refluxed for 18 hours, cooled, and concentrated. The residue was suspended in 25 mL of 1N sodium hydroxide and heated at 80° C. for 90 minutes. The clear yellow solution was cooled to room temperature, filtered, and neutralized (pH 6.8) with 6N hydrochloric acid. The solids were filtered, washed with water and ether, and dried to give 0.32 g of the title compound, mp 222°–225° C.

The following compound was prepared in identical fashion:
a) 6,8-Difluoro-1,4-dihydro-5-methyl-7-(3-methyl-1-piperazinyl)-1-vinyl-3-quinolinecarboxylic acid, mp 232°–235° C.

Example 17

6-Fluoro-1-(2,4-difluorophenyl)-1,4-dihydro-5-methyl-4-oxo-7-(1-piperazinyl)-3-quinolinecarboxylic acid A solution of 0.76 g (2.00 mmol) of ethyl 6,7-difluoro-1-(2,4-difluorophenyl)-1,4-dihydro-5-methyl-4-oxo-3-quinolinecarboxylate, 0.69 g (8.00 mmol) of anhydrous piperazine, and 30 mL of acetonitrile was refluxed for 18 hours, cooled, and concentrated. The residue was dissolved in 20 mL 6N hydrochloric acid and refluxed for 3 hours. The suspension was cooled, concentrated by half and filtered, and the solids were washed with water. The crude product was suspended in water which was made basic (pH 12), and the resulting solution was filtered and neutralized to pH 6.8. The precipitate which formed was filtered, washed with water, and dried to give 0.58 g of the title compound, mp 198°–200° C.

The following compounds were also prepared by following essentially the same procedure:
a) 6-Fluoro-1-(2,4-difluorophenyl)-1,4-dihydro-5-methyl-7-(3-methyl-1-piperazinyl)-4-oxo-3-quinolinecarboxylic acid, mp 188°–191° C.;
b) 6-Fluoro-1-(2,4-difluorophenyl)-1,4-dihydro-5-methyl-7-(3, 5-dimethyl-1-piperazinyl)-4-oxo-3-quinolinecarboxylic acid, mp 213°–215° C.;
c) 7-(3-Amino-1-pyrrolidinyl)-6-fluoro-1-(2,4-difluorophenyl)-1,4-dihydro-5-methyl-4-oxo-3-quinolinecarboxylic acid, mp 232°–234° C.;
d) 7-[3-(Ethylamino)methyl-1-pyrrolidinyl]-6-fluoro-1-(2, 4-difluorophenyl)-1,4-dihydro-5-methyl-4-oxo-3-quinolinecarboxylic acid, mp 196°–198° C.; and
e) 7-[3-(Aminomethyl)-3-methyl-1-pyrrolidinyl]-6-fluoro-1(2,4-difluorophenyl)-1,4-dihydro-5-methyl-4-oxo-3-quinolinecarboxylic acid, mp 181°–184° C.

Example 18

7-(3-Amino-1-pyrrolidinyl)-1-cyclopropyl-6-fluoro-1,4-dihydro-5-methyl-4-oxo-1,8-naphthyridine-3-carboxylic acid Triethylamine (0.17 mL, 1.2 mmol), 3-(t-butoxycarbonylamino) pyrrolidine (0.22 g, 2.1 mmol) and 0.39 g (1.2 mmol) of 7-chloro-1-cyclopropyl-6- fluoro-1,4-dihydro-5-methyl-4-oxo-1,8-naphthyridine-3-carboxylic acid ethyl ester were dissolved in acetonitrile (10 mL) and the mixture heated to reflux for 4 hours, then cooled and diluted with ether (50 mL). This solution was washed with saturated solutions of $KHCO_3$ and NaCl and dried over $Na_2SO_4$. It was necessary to add $CH_2Cl_2$ to maintain a homogeneous solution. After filtration and evaporation the residue was dissolved in ether and allowed to stand. The crystals that formed were collected by filtration to give 0.56 g of the intermediate ester. This ester was dissolved in acetic acid (15 mL) and 6N HCl (1 mL) was added and the mixture heated to reflux for 2 hours, then evaporated to a gum. This gum was dissolved in ethanol (10 mL), and 5N NaOH (2 mL) was added and the mixture stirred for 2 hours. The reaction was evaporated to a gum and dissolved in water (60 mL) to give a solution at pH 12. The pH was adjusted to 6.5 and the solid formed collected and washed with water and dried to give the title compound (0.38 g).

Example 19

1-Cyclopropyl-6-fluoro-1,4-dihydro-5-methyl-4-oxo-7-(1-piperazinyl)-1,8-naphthyridine-3-carboxylic acid The procedure used in Example 18 was employed to prepare the title compound in 58% yield.

Example 20

1-Ethyl-6-fluoro-1,4-dihydro-5-methyl-4-oxo-1-(piperazinyl)-3-quinolinecarboxylic acid A suspension of 0.67 g (2.50 mmol) of 1-ethyl-6,7-difluoro-1,4-dihydro-5-methyl-4-oxo-3-quinolinecarboxylic acid, 0.86 g (10.0 mmol) of anhydrous piperazine, and 25 mL of acetonitrile was refluxed for 6 hours, then cooled to room temperature. The solids were filtered, washed with water and ether, and dried to give 0.58 g of the title compound, mp 225°–227° C.

The following compounds were prepared by following essentially the same procedure as described above:
a) 1-Ethyl-7-[3-[(ethylamino)methyl]-1-pyrrolidinyl]-6-fluoro-1,4-dihydro-5-methyl-4-oxo-3-quinolinecarboxylic acid, mp 180°–182° C.
b) 7-(3-Amino-1-pyrrolidinyl)-1-ethyl-6-fluoro-1,4-dihydro-5-methyl-4-oxo-3-quinolinecarboxylic acid, mp 210°–213° C.
c) 1-Ethyl-6-fluoro-1,4-dihydro-5-methyl-7-(3-methyl-1-piperazinyl)-4-oxo-3-quinolinecarboxylic acid, mp 228°–231° C.
d) 1-Ethyl-6-fluoro-1,4-dihydro-5-methyl-7-3,5-dimethyl-1-piperazinyl)-4-oxo-3-quinolinecarboxylic acid, mp 219°–221° C.
e) 7-[3-(Aminomethyl)-3-methyl-1-pyrrolidinyl]-1-ethyl-6-fluoro-1,4-dihydro-5-methyl-4-oxo-3-quinolinecarboxylic acid, mp 223°–225° C.

Example 21

7- [3-(Endo-amino)-8-azabicyclo[3.2.1 ]oct-8-yl]-8-chloro-1-cyclopropyl-6-fluoro-1,4-dihydro-5-methyl-4-oxo-3-quinolinecarboxylic acid A mixture of 0.50 g (1.6 mmol) of 8-chloro-1-cyclopropyl-6,7-difluoro-1,4-dihydro-5-methyl-4-oxo-3-quinolinecarboxylic acid, 0.36 g (1.8 mmol) of 3-(endo-amino)-8-azabicyclo [3.2.1]octane dihydrochloride, 0.72 mL (4.8 mmol) of 1,8-diazabicyclo[5.4.0]undec-7-ene and 15 mL of acetonitrile was heated at reflux for 18 hours. The suspension was cooled to room temperature, diluted with ether, and refrigerated. The resulting solid was filtered, washed with ethanol and ether, and dried to give the title compound.

The following compounds were prepared in identical fashion:

Example a. 7-[3-(endo-amino)-8-azabicyclo[3.2.1]=oct-8-yl]-6,8-difluoro-1-(2,4-difluorophenyl)-1,4-dihydro-5-methyl-4-oxo-3-quinolinecarboxylic acid.

Example b. 7-[3-(endo-amino)-8-azabicyclo[3.2.1]-oct-8-yl]-1-cyclopropyl-6, 8-difluoro-1,4-dihydro-5-methyl-4-oxo-3-quinolinecarboxylic acid.

Example 22

7-(3-Amino-1-pyrrolidinyl)-1-(2,4-difluorophenyl)-6-fluoro-1,4-dihydro-5-methyl-4-oxo-1,8-naphthyridine-3-carboxylic acid A mixture of 0.7 g (2 mmole) of the product from Example XX, 0.6 mL (4 mole) triethylamine, 0.5 g (2.5 mmole) 3-(t-butoxycarbonylamino) pyrrolidine and 15 mL acetonitrile was refluxed for 1 hour. The mixture was concentrated in vacuo and purified by column chromatography (silica gel dichloromethane/ethanol 97:3) to yield 0.6 g of the fully protected title compound. The product was dissolved in 15 mL acetic acid and 15 mL 6N HCl and heated to reflux for 10 hours. The solvent was removed by evaporation in vacuo and the residue was dissolved in $H_2O$ with dilute NaOH. The filtered solution was neutralized to a pH 7 with dilute HCl. The product was collected by filtration and washed with $H_2O$, acetonitrile, and ether to afford 0.36 g of the title compound, mp 260° C.

Analyses for $C_{20}H_{17}H_4O_3F_3 \cdot 1.5\ H_2O$:
Calcd.: C, 53.92; H, 4.49; N, 12.57; Found: C, 54.10; H, 4.27; H, 12.20.

Example 23

3R, 1'S-7-[3-(1-Aminoethyl)-1-pyrrolidinyl]-1-(2,4-difluorophenyl)-6-fluoro-1,4-dihydro-5-methyl-4-oxo-1,8-naphthyridine carboxylic acid A solution of 0.67 g (2.9 mole) of the compound from Example XX, 0.8 g (3.1 mole) 3R, 1'S-3-(1-(t-butoxycarbonyl)aminoethyl)pyrrolidine, 1.2 mL (8.6 mmole) triethylamine and 15 mL acetonitrile was heated to reflux for 1 hour. The mixture was concentrated in vacuo and the residue was purified by column chromatography (silica gel dichloromethane/ethanol 97: 3) to yield 0.9 g of the fully protected title compound. The compound was refluxed in a solution of 15 mL acetic acid and 15 mL of 6N hydrochloric acid for 8 hours and evaporated in vacuo. The residue was dissolved in H20 with dilute NaOH, filtered, and neutralized with dilute hydrochloric acid to a final pH of 7. The product was collected by filtration, washed with $H_2O$, dissolved in 6N HCl, diluted with $H_2O$, and concentrated to dryness. Recrystallization from isopropyl alcohol/diethyl ether afforded 0.37 g of the title compound as the HCl salt, mp 297°-299° C.

Analysis for $C_{22}H_{21}N_4O_6F_3 \cdot 0.3\ H_2O \cdot 1.0\ HCl$:
Calcd.: C, 54.11; H, 4.66; N, 11.46; Found: C, 54.01; H, 4.68; N, 11.40.

Example 24

3R, 1'S-7-[3-(1-(N-Methylamino)ethyl)-1-pyrrolidinyl]-1-(2,4-difluorophenyl)-6-fluoro-1,4-dihydro-5-methyl-4-oxo-1,8-naphthyridine-3-carboxylic acid In 15 mL acetonitrile, the product from Example XX, 0.5 g (1.5 mole) along with 0.65 mL (4.6 mole) triethylamine, and 0.45 g (1.7 mmole) 3R, 1'S-3-[1-(t-butoxycarbonyl)methylaminoethyl]pyrrolidine was heated to reflux for 1 hour. After removal of the solvents in vacuo, the residue was purified by column chromatography (silica gel dichloromethane/ethanol 95:5) to yield 0.6 g of the fully protected title compound. Deprotection was achieved by refluxing the above compound in a mixture of 15 mL acetic acid and 15 mL 6N hydrochloric acid for 28 hours. The solvents were removed in vacuo and the product dissolved in $H_2O$ using dilute NaOH. The filtered solution was neutralized with dilute hydrochloric acid to a pH 7. The product was collected by filtration and washed with $H_2O$. The solid was dissolved in concentrated hydrochloric acid, diluted with $H_2O$, and concentrated in vacuo. The residue was recrystallized from isopropanol/diethyl ether to yield 0.3 g of the title compound as the hydrochloric salt, mp 280° C. dec. Analyzed for $C_{23}H_{23}N_4O_3F_3 \cdot 0.2\ H_2O \cdot 1.0\ HCl$: Calcd.: C, 55.18; H, 4.91; N, 11.19; Found: C, 55.05; H, 4.71; N, 10.93.

Example 25

3R-7-[3-(1-Amino-1-methylethylpyrrolidin-1-yl]-1-(2,4-difluorophenyl)-6-fluoro-1,4-dihydro-5-methyl-4-oxo-1,8-naphthyridine-3-carboxylic acid A mixture of 0.33 g (1 mole) of the product from Example XX, 0.30 g (1.1 mole) 3R-(1-(t-butoxycarbonylamino)-1-methylethyl)pyrrolidine hydrochloride, 0.42 mL (7 mmole) triethylamine and 20 mL acetonitrile was heated to reflux for a total of 3 hours. The crude mixture was concentrated in vacuo, dissolved in 20 mL acetic acid/20 mL 6N hydrochloric acid, and heated to reflux for 28 hours. After removal of the solvents in vacuo, the crude product was dissolved in $H_2O$ with dilute NaOH, filtered, and the solution was neutralized with dilute HCl to a final pH 6.8. The product was collected by filtration and washed with $H_2O$. The solid was dissolved in concentrated hydrochloric acid, diluted with $H_2O$ and evaporated to dryness. Recrystallization from isopropyl alcohol/ether afforded 0.23 g of the title compound as the HCl salt, mp 230°–233° C. Analyzed for $C_{23}H_{23}N_4O_3F_3 \cdot 0.9\ H_2O \cdot 1.0\ HCl$: Calcd.: C, 53.83; H, 5.06; N, 10.91; Found C, 53.83; H, 5.23; N, 10.61.

Example 26

3S-7-[3-Amino-1-pyrrolidinyl]-1-(2,4-difluorophenyl)-6-fluoro-1,4-dihydro-5-methyl-4-oxo-1,8-naphthyridine-3-carboxylic acid A mixture of 0.80 g (2.2 mmole) of the product of Example XX, 0.53 g (2.8 mmole) of S-3-(t-butoxycarbonyl) aminopyrrolidine, 0.9 mL (6.4 mmole) triethyl amine, and 20 mL acetonitrile was heated to reflux for 3 hours. After concentration in vacuo the residue was purified by column chromatography (silica gel dichloromethane/ethanol 95:5) to yield 0.85 g of the fully protected title compound. The compound was heated to reflux in a solution of 20 mL acetic acid and 20 mL 6N hydrochloric acid for 16 hours. After concentration in vacuo the product was dissolved in $H_2O$ with dilute aqueous NaOH, filtered, and the solution was neutralized with dilute hydrochloric acid to a final pH of 7. The product was collected by filtration and washed with $H_2O$. The solid was dissolved in concentrated hydrochloric acid, diluted with $H_2O$, and evaporated to dryness. Recrystallization from isopropyl alcohol/ether afforded 0.57 g of the title compound as the HCl salt, mp 210°–211° C.

Example 27

7-[(3-N-Ethylaminomethyl)pyrrolidin-1-yl]-1-cyclopropyl-6-fluoro-1,4-dihydro-5-methyl-4-oxo-1,8-naphthyridine-3-carboxylic acid A solution of 0.7 g (2 mmole) of the product from Example ZZ, 0.4 g (3.1 mmole) of 3-N-ethylpyrrolidinemethanamine, 0.85 mL (6.1 mmole) triethylamine, and 20 mL acetonitrile was heated to reflux for a total of 8 hours. After concentration in vacuo, the compound was partially purified by column chromatography (silica gel-dichloromethane/ethanol/triethylamine 94:3:1) to yield 1.1 g. This residue was dissolved in 20 mL methanol/5 mL H$_2$O and treated with 4 mL of 1N NaOH. After stirring at room temperature for 3.5 hours, the methanol was removed in vacuo, and the mixture diluted with H$_2$O, and the solution was extracted once with dichloromethane. After filtration, the basic aqueous layer was neutralized with dilute hydrochloric acid to a final pH of 7. The product was collected by filtration and washed with H$_2$O, ether, and dried to afford 0.55 g of the title compound, mp 157°–66° C. Analyzed for C$_{20}$H$_{25}$N$_4$O$_3$F.0.7 H$_2$O: Calcd.: C, 59.81; H, 6.58; N, 13.97; Found: C, 59.73; H, 6.51; N, 14.08.

Example 28

7-(3-Aminomethylpyrrolidin-1-yl)-1-cyclopropyl-6-fluoro-1,4-anhydro-5-methyl-4-oxo-1,8-naphthyridine carboxylic acid A mixture of the product of Example ZZ, 0.7 g (2 mole), 0.85 mL (6 mole) triethylamine, 0.48 g (2.4 mmole) 3-(t-butoxycarbonyl) aminomethylpyrrolidine and 30 mL acetonitrile was heated to reflux for a total of 4 hours. The solvent was removed in vacuo and the crude residue was heated to reflux in a solution of 15 mL acetic acid/15 mL 6N HCl for a total of 24 hours. The solvent was removed in vacuo and the residue was dissolved in H$_2$O with dilute NaOH. The filtered solution was neutralized with dilute hydrochloric acid to a final pH of 7. The precipitate formed was collected by filtration to afford 0.24 g of the title compound, mp>285° C.

We claim:
1. A compound of formula

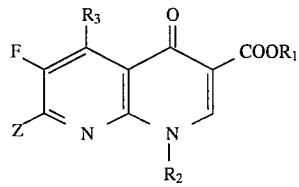

or a pharmaceutically acceptable acid addition or base salt thereof wherein Z is

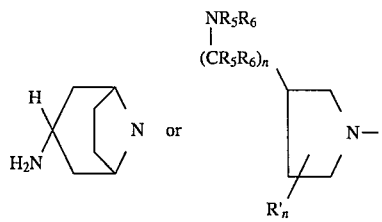

wherein
R$_1$ is hydrogen, alkyl of from one to six carbon atoms, or a cation;
R$_2$ is alkyl of from one to four carbon atoms, vinyl, haloalkyl, hydroxyalkyl of from two to four carbon atoms, cycloalkyl of from three to six carbon atoms, phenyl or phenyl substituted by halogen, alkyl, NH$_2$ or OH;
R$_3$ is lower straight, branched, or cyclic alkyl of from one to three carbon atoms;
R$_5$ and R$_6$ are each independently hydrogen, lower alkyl or cycloalkyl;
R' is hydrogen, hydroxyl, alkyl of from one to four carbon atoms, phenyl or phenyl substituted by halogen, alkyl, or alkoxy; and n is an integer of from 0 to 4.
2. A compound according to claim 1, wherein R$_2$ is cyclopropyl, ethyl or 2,4-difluorophenyl.
3. A compound according to claim 1, wherein R$_3$ methyl, ethyl, isopropyl, or cyclopropyl.
4. A compound according to claim 1, wherein R$_1$ is hydrogen.
5. A compound according to claim 1, wherein Z is selected from the group consisting of:

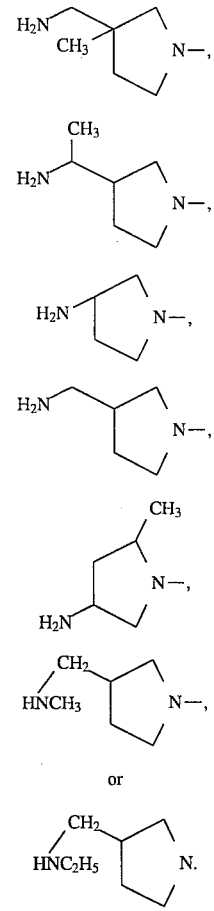

or

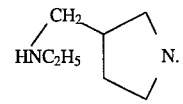

6. A compound according to claim 1 selected from:
1-cyclopropyl-7-(3-amino-1-pyrrolidinyl)-6-fluoro-5-methyl-1,4-dihydro-4-oxo-1,8-naphthyridine-3-carboxylic acid ethyl ester,
7-(3-amino-1-pyrrolidinyl)-1-(2,4-difluorophenyl)-6-fluoro-1,4-dihydro-5-methyl-4-oxo-1,8-naphthyridine-3-carboxylic acid,
3R,1'S-7-[3-(1-amino-ethyl)-1-pyrrolidinyl]-1-(2,4-difluorophenyl)-6-fluoro-1,4-dihydro-5-methyl-4-oxo-1,8-naphthyridine-3-carboxylic acid,
3R,1'S-7-[3-(1-N-methylamino)ethyl]-1-pyrrolidinyl]-1-(2,4-difluorophenyl)-6-fluoro-1,4-dihydro-5-methyl-4-oxo-1,8-naphthyridine-3-3carboxylic acid,
3R-7-[3-(1-amino-1-methylethylpyrrolidin-1-yl]-1-(2,4-difluorophenyl)-6-fluoro-1,4-dihydro-5-methyl-4-oxo-1,8-naphthyridine-3-carboxylic acid,
3S-7-[3-amino-1-pyrrolidinyl]-1-(2,4-difluorophenyl)-6-fluoro-1,4-dihydro-5-methyl-4-oxo-1,8-naphthyridine-3-carboxylic acid,
7-[(3-N-ethylaminomethyl)pyrrolidin-1-yl]-1-cyclopropyl-6-fluoro-1,4-dihydro-5-methyl-4-oxo-1,8-naphthyridine-3-carboxylic acid, and 7-(3-aminomethylpyrrolidin-1-yl)-1-cyclopropyl-6-fluoro-1,4-dihydro-5-methyl-4-oxo-1,8-naphthyridine carboxylic acid.

7. A pharmaceutical composition comprising an antibacterially effective amount of compound according to claim 1 together with a pharmaceutically acceptable carrier.

8. A method of treating bacterial infections in mammals, which comprises administering to said mammal an effective amount a compound according to claim 1.

9. A process for the preparation of a compound of claim 1, which comprises reacting a compound of formula

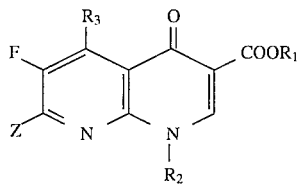

wherein L is fluorine or chlorine with an amine corresponding to Z as defined in claim 1 and, optionally converting the resulting product to a pharmaceutically acceptable acid addition or base salt thereof.

10. A process for the preparation of a compound of claim 1, which comprises the steps of (a) reacting a compound of formula

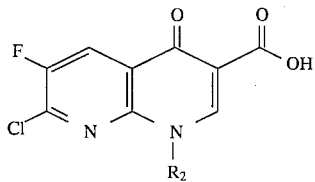

with oxalyl chloride and dimethylformamide and quenching with alcohol to produce the corresponding ester

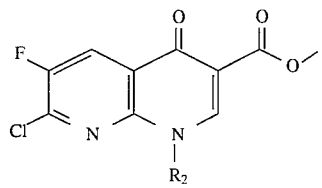

(b) reducing the double bond to produce a compound of formula

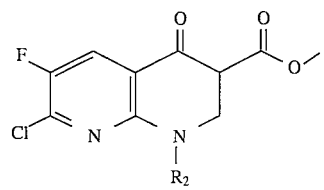

(c) treating the compound from step (b) with a base, then methyl iodide to produce the alkylated compound

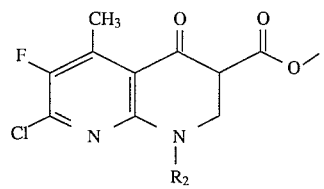

(d) reintroducing the double bond and reacting the resulting naphthyridine with an amine corresponding to Z as defined in claim 1.

* * * * *

UNITED STATES PATENT AND TRADEMARK OFFICE
CERTIFICATE OF CORRECTION

PATENT NO. : 5,585,491
DATED : December 17, 1996
INVENTOR(S) : John M. DOMAGALA et al.

It is certified that error appears in the above-indentified patent and that said Letters Patent is hereby corrected as shown below:

Claim 9, column 55, lines 12-19, in the formula,

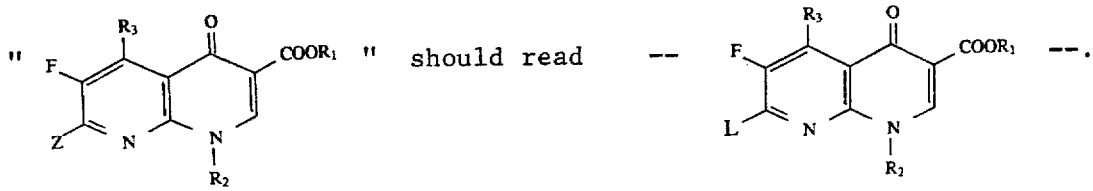

Signed and Sealed this

Twenty-fourth Day of June, 1997

Attest:

BRUCE LEHMAN

Attesting Officer

Commissioner of Patents and Trademarks